United States Patent
Turcott

(10) Patent No.: US 7,177,686 B1
(45) Date of Patent: Feb. 13, 2007

(54) USING PHOTO-PLETHYSMOGRAPHY TO MONITOR AUTONOMIC TONE AND PERFORMING PACING OPTIMIZATION BASED ON MONITORED AUTONOMIC TONE

(75) Inventor: Robert Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 488 days.

(21) Appl. No.: 10/764,419

(22) Filed: Jan. 23, 2004

Related U.S. Application Data

(63) Continuation-in-part of application No. 10/208,081, filed on Jul. 29, 2002, now Pat. No. 6,942,622, which is a continuation-in-part of application No. 09/467,298, filed on Dec. 17, 1999, now Pat. No. 6,480,733, which is a continuation-in-part of application No. 09/438,017, filed on Nov. 10, 1999, now Pat. No. 6,409,675.

(51) Int. Cl.
*A61N 1/365* (2006.01)
*A61B 5/0295* (2006.01)

(52) U.S. Cl. .......... 607/23; 600/485; 600/500; 600/508

(58) Field of Classification Search .......... None
See application file for complete search history.

(56) References Cited

U.S. PATENT DOCUMENTS

| | | | |
|---|---|---|---|
| 4,869,254 A | 9/1989 | Stone et al. ........... 128/633 |
| 5,078,136 A | 1/1992 | Stone et al. ........... 128/633 |
| 5,269,310 A * | 12/1993 | Jones et al. .......... 600/480 |
| 5,312,452 A | 5/1994 | Salo ..................... 607/17 |
| 5,334,222 A | 8/1994 | Salo et al. ............. 607/17 |
| 5,466,245 A | 11/1995 | Spinelli et al. ......... 607/17 |
| 5,487,752 A | 1/1996 | Salo et al. ............. 607/17 |
| 5,540,727 A | 7/1996 | Tockman et al. ........ 607/18 |
| 5,694,939 A * | 12/1997 | Cowings ............... 600/484 |
| 5,800,471 A | 9/1998 | Baumann ............... 607/25 |
| 6,162,188 A * | 12/2000 | Barnea ................. 600/587 |
| 6,409,675 B1 | 6/2002 | Turcott ................ 600/508 |
| 6,480,733 B1 | 11/2002 | Turcott ................ 600/516 |
| 6,491,639 B1 | 12/2002 | Turcott ................ 600/508 |
| 6,522,923 B1 | 2/2003 | Turcott ................ 607/27 |
| 6,567,700 B1 | 5/2003 | Turcott et al. ........... 607/9 |
| 6,575,912 B1 | 6/2003 | Turcott ................ 600/485 |
| 2001/0031993 A1 | 10/2001 | Salo et al. ............... 607/9 |
| 2003/0097158 A1 | 5/2003 | Belalcazar ............. 607/32 |

OTHER PUBLICATIONS

Curtis, et al., "Autonomic Tone as a Cardiovascular Risk Factor: The Dangers of Chronic Fight or Flight" Mayo Clin Proc, Jan. 2002; vol. 77, pp. 45-54.

* cited by examiner

*Primary Examiner*—Carl Layno
(74) *Attorney, Agent, or Firm*—Steven M. Mitchell

(57) ABSTRACT

The autonomic tone of a patient is measured based on a photo-plethysmography signal that is representative of arterial pulse pressure of the patient. Such measures of autonomic tone can be used to monitor the hemodynamic status of a patient, and even to perform pacing interval optimization. Further embodiments relate to pacing interval optimization performed based on a signal indicative of cardiac contractions of a patient's heart, as the patient's heart is paced using different sets of pacing interval parameters. Such a signal can be a photo-plethysmography signal or an alternative type of signal. Measures of pulse amplitude are obtained from the signal, and pacing interval optimization is performed based on the measures of pulse amplitude.

39 Claims, 27 Drawing Sheets

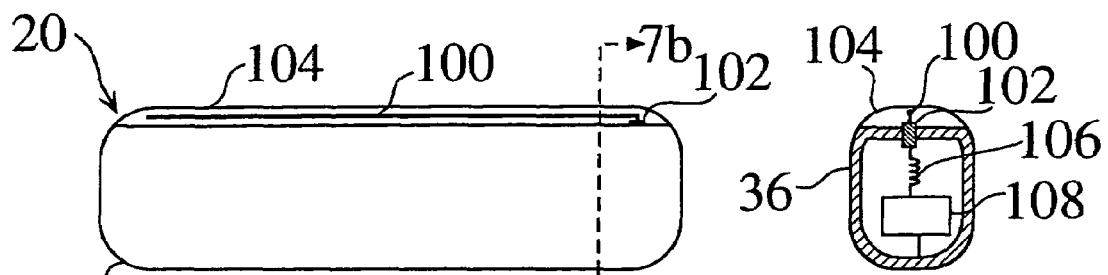
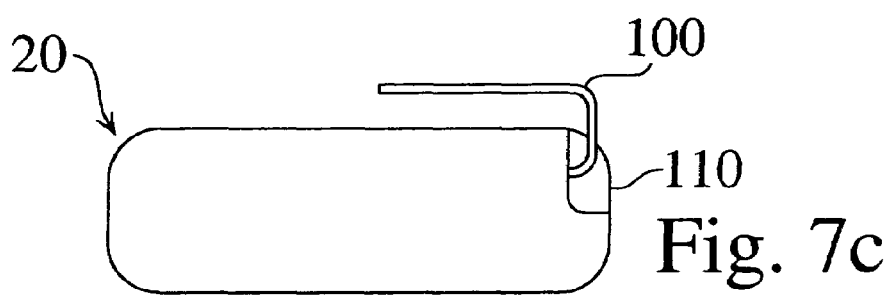
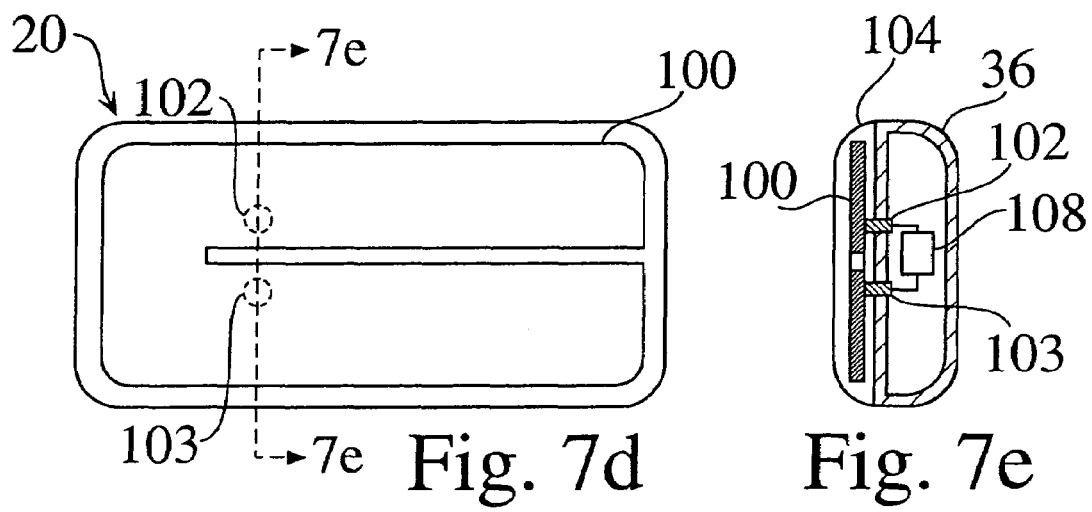
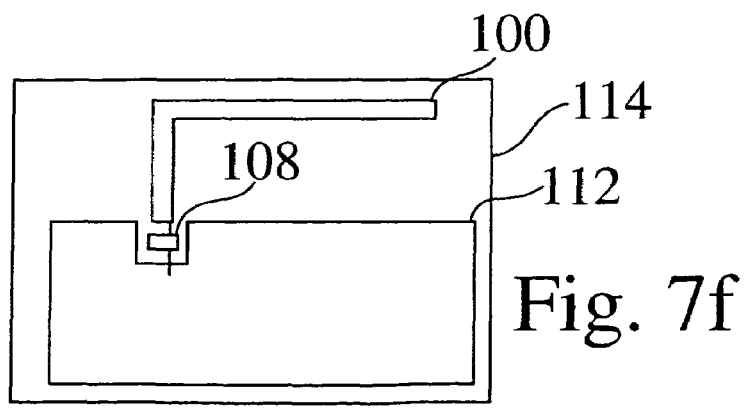

USING PHOTO-PLETHYSMOGRAPHY TO MONITOR AUTONOMIC TONE AND PERFORMING PACING OPTIMIZATION BASED ON MONITORED AUTONOMIC TONE

PRIORITY CLAIM

This application is a continuation-in-part of U.S. patent application Ser. No. 10/208,081 filed Jul. 29, 2002, (now U.S. Pat. No. 6,942,622), which is a continuation-in-part of U.S. patent application Ser. No. 09/467,298, filed Dec. 17, 1999 (now U.S. Pat. No. 6,480,733), which is a continuation-in-part of application Ser. No. 09/438,017, filed Nov. 10, 1999 (now U.S. Pat. No. 6,409,675), each of which is incorporated herein by reference.

FIELD OF THE INVENTION

Embodiments of the present invention relate to monitoring cardiac performance, as well as performing pacing optimization based on monitored cardiac performance.

BACKGROUND OF THE INVENTION

The multiplicity of feedback mechanisms that influence cardiac performance places the heart at the center of a complex control network. The neurohumoral axis includes the autonomic nervous system, consisting of sympathetic and parasympathetic branches, and numerous circulating hormones such as catacholamines, angiotensin, and aldosterone. Neural reflex arcs originating from pressure and stretch receptors, which directly measure mechanical hemodynamic status, modulate the neurohumoral axis. Similarly, chemoreceptors respond to changes in $CO_2$, pH, and $O_2$, which assesses cardiopulmonary function. The neurohumoral system influences cardiac performance at the level of the cardiac electrical system by regulating heart rate and the conduction velocity of electrical depolarizations. It also influences cardiac performance at the mechanical level, by controlling contractility, that is, the effective vigor with which the heart muscle contracts. Conventional cardiac monitors, such as defibrillators, pacemakers, Holter monitors, and cardiac event records, are tailored for the diagnosis and/or therapy of abnormalities of the cardiac electrical system. In contrast, heart failure is a disease of the cardiac mechanical system: it is primarily a failure of the myocardium to meet the mechanical pumping demands required of it. In monitoring the status of a heart failure patient, measuring the mechanical hemodynamic variables is clearly desirable. Examples of mechanical hemodynamic variables include atrial, ventricular, and arterial pressures, and cardiac output (volume of blood pumped into the aorta per unit time). However, because of the complex feedback network that monitors and controls cardiac performance, measuring variables that do not directly reflect the mechanical performance of the heart is also useful. In this way, measuring cardiac electrical activity to assess heart rate variability (described below) allows one to infer the state of the autonomic nervous system, which allows one to infer information about the hemodynamic status of a heart failure patient. Similarly, recognition of Cheyne-Stokes respiration (described below) via respiratory pattern analysis, hemoglobin saturation analysis, and blood gas analysis allows one to detect the presence of pulmonary edema, and thereby detect an acute heart failure exacerbation, though none of these parameters directly measure mechanical hemodynamic status. It would be useful to provide additional and/or alternative ways for monitoring the state of a patient's autonomic nervous system, which are not dependent on heart rate.

One approach to frequent monitoring of heart failure patients that has been proposed is the daily acquisition of the patient's weight and responses to questions about subjective condition (Alere DayLink Monitor, Alere Medical, Inc., San Francisco, Calif.). The simplicity and noninvasive embodiment of this approach are desirable features. However, both the amount and the sophistication of the objective physiological data that can be acquired in this way are quite limited, which consequently limits the accuracy of the system. Furthermore, the system requires the active participation of the patient, who must not deviate from the precise data acquisition routine or risk introducing confounding factors into the acquired data.

Some of these limitations have been addressed by the development of an implantable system that monitors hemodynamic status (Medtronic Chronicle, Medtronic, Inc., Minneapolis, Minn.). While this system potentially avoids the need for active patient participation, it relies on an intravascular sensor placed in the right ventricle of the heart. This approach is consistent with the prior art for implantable hemodynamic status monitoring, which has to date focused on intravascular or intramyocardial instrumentation. Examples include U.S. Pat. No. 5,454,838 in which Vallana et al. teach placement of a sensor on the myocardial wall using an intravascular approach. In U.S. Pat. No. 5,496,351, Plicchi et al. propose placing a sensor within the myocardial wall. Mortazavi in U.S. Pat. No. 5,040,538 and Cohen et al. in U.S. Pat. No. 4,815,469 describe placement of an optical sensor within the right ventricle. In the context of hemodynamic assessment for arrhythmia discrimination, Cohen and Liem (*Circ.*, 1990, 82:394–406) study the effectiveness of a pressure transducer placed in the right ventricle. Clearly, powerful information about hemodynamic status can be obtained using intravascular instrumentation. However, intravascular or intramyocardial instrumentation carries significant risks to the patient, including increased perioperative morbidity and mortality, and increased long-term risks such as stroke and pulmonary embolism. Furthermore, intravascular instrumentation can only be performed by extensively trained specialists, thereby limiting the availability of qualified physicians capable of implanting the device, and increasing the cost of the procedure. Finally, because of the added patient risks and greater physical demands of an intravascular environment, the intravascular placement of the sensor increases the cost of development, manufacturing, clinical trials, and regulatory approval.

Though not directly related to hemodynamic status monitoring, extravascular sensing of cardiac electrical activity is known in the art. Early generations of implantable pacemakers and defibrillators relied on epicardial placement of sensing electrodes. Epicardial electrodes still see use in special patient populations. Extrathoracic sensing of cardiac electrical activity is also possible, which avoids the need for direct contact with the heart, and thus decreases the difficulty of the implant procedure and reduces the risk of perioperative complications. An example of this approach is the Reveal Insertable Loop Recorder (Medtronic, Inc., Minneapolis, Minn.), a cardiac event recorder configured for short-term implantation. As a temporarily implantable recorder, it overcomes some of the technical difficulties associated with conventional externally worn recorders of cardiac electrical activity. Two general types of externally worn recorders are Holter monitor recorders, which record continuously for an extended period of time, and cardiac event recorders, such as the King of Hearts (Alaris Medical Systems, San Diego, Calif.), which use a loop memory to retain the most recent history of cardiac electrical activity. Both these approaches require surface contact electrodes which are cumbersome and inconvenient for the patient, and more susceptible to motion artifact than an implanted electrode. However, like conventional cardiac event recorders and continuous Holter monitor recorders, the Reveal Insertable Loop Recorder is designed for short-term use as a diagnostic aid. More importantly, it requires active patient participation; when the patient recovers from syncope, or becomes aware of symptoms, he must signal to the event recorder by means of an Activator that the recent data should be retained in long-term memory for later review by a physician. After diagnosis the Reveal Insertable Loop Recorder is explanted from the patient. Thus the Reveal is intended for short-term recording for diagnostic use, is limited to recording the electrical activity of the heart, and does not attempt to measure or quantify the hemodynamic status of the patient beyond screening for cardiac arrhythmias.

An extension of the short-term recorders just described is the Implantable Ambulatory Electrocardiogram Monitor described by Nappholz et al. in U.S. Pat. No. 5,113,869, incorporated herein by reference. This device is designed for chronic extravascular implantation. In contrast to cardiac recorders, it performs analysis on the electrocardiogram signal in order to predict imminent cardiac arrhythmias and to detect cardiac ischemia. Like the cardiac recorders, it is capable of storing raw ECG data for later review by a physician. This feature, along with the record of arrhythmic events it detected, allows the physician to tailor pharmacologic therapy. In addition, Nappholz et al. mention the use of transthoracic impedance for minute ventilation, ultrasound transducers for arterial pressure, or other sensors to allow discrimination of arrhythmias from normal cardiac rhythms caused by exertion or physiologic stress.

While the Holter monitor recorder, the Reveal Insertable Loop Recorder, and the Implantable Ambulatory Electrocardiogram Monitor provide important clinical utility in recording and monitoring cardiac electrical activity, none is designed to monitor hemodynamic status. Indeed, cardiac electrical activity does not, by itself, provide unambiguous information about hemodynamic status. By sensing only cardiac electrical activity, these devices are unable to distinguish between, for example, a hemodynamically stable cardiac rhythm and Pulseless Electrical Activity (PEA), a condition in which the heart is depolarizing normally, and thus generating a normal electrical pattern, but is not pumping blood. Furthermore, these devices are unable to recognize or quantify subtle changes in the patient's hemodynamic status. What is needed is an extravascular, hemodynamic monitor designed for chronic use.

While much of the prior art has focused on intravascular instrumentation, as discussed above, some proposal has been made to incorporate physiologic sensors into the implantable cardiac device itself. Fearnot in U.S. Pat. No. 5,040,533 teaches placement of a generalized window in the housing of the cardiac device. The window might be transparent to facilitate the transmission of light or flexible to facilitate pressure transduction. While the convenience, from the clinician's perspective, of incorporating the sensors into the housing of the cardiac device is an obvious advantage, the technical difficulty in maintaining a hermetic seal between two different materials, particularly in a chronically implanted device, is equally obvious to one skilled in the art. The technical challenge is made more difficult by the greatly increased circumference, relative to that of standard feed-through connections known in the art, of the boundary between the window and the device housing. What is needed, therefore, is a method of placing a hemodynamic sensor in or on the device without compromising the integrity of the hermetic enclosure.

Prutchi et al., in U.S. Pat. No. 5,556,421 propose placement of a sensor within the header of a cardiac device. While this is an obvious solution for devices that have external leads requiring headers, it presupposes the existence of a header, and therefore does not address the implantable device that lacks a header. Furthermore, while appending a header to one end or pole of an implantable device is an efficient solution when external leads are required, appending a header-like sensor unit to one end or pole of a device not otherwise requiring a header, where the sensor unit is itself, like a header, the full-thickness of the device, is an inefficient use of volume. Thus, the approach of Prutchi et al. used in a device that doesn't otherwise require a header would be to append a header or a header-like sensor unit to one end or pole of the device, but this would unnecessarily increase both the volume and the expense of the device. A further disadvantage of placing a sensor in a header is that it does not necessarily provide for the optimal signal transduction of a particular sensor. For example, the performance of the optical sensor described in the above referenced U.S. Pat. No. 5,556,421 would be so severely degraded by direct transmission of light from source to detector that one skilled in the art would question the functionality of the proposed solution. In addition, placement in a rigid epoxy header is simply not an option for some sensors, such as sound sensors, because of the dramatic degradation in the signal-to-noise ratio the rigid header would impose. What is needed is a method of incorporating a hemodynamic sensor into a implantable device, providing it optimal access to the external milieu so that the signal of interest is optimally transduced, maintaining the hermetic enclosure provided by the device housing, and minimizing the added volume that the sensor imposes. In addition to improving hemodynamic sensors, it would also be useful to provide new uses for such sensors.

BRIEF SUMMARY OF THE INVENTION

Embodiments of the present invention are directed toward monitoring the autonomic tone of a patient, based on a photo-plethysmography signal that is representative of arterial pulse pressure of the patient. Embodiments of the present invention are also directed toward performing pacing interval optimization, based on the monitored of autonomic tone.

Embodiments of the present invention are also directed to performing pacing interval optimization by producing a signal indicative of cardiac contractions of a patient's heart, as the patient's heart is paced using different sets of pacing interval parameters. Such a signal can be a photo-plethysmography signal or an alternative type of signal. Measures of pulse amplitude are obtained from the signal, and pacing interval optimization is performed based on the measures of pulse amplitude.

Further embodiments, objects and advantages of the various embodiments of the present invention will become apparent from a consideration of the ensuing description and drawings.

BRIEF DESCRIPTION OF THE SEVERAL VIEWS OF THE DRAWINGS

FIGS. 7a–7f provide various views of the preferred and alternate embodiments of the telemetry system of invention;

DETAILED DESCRIPTION OF THE INVENTION

Figure 1:
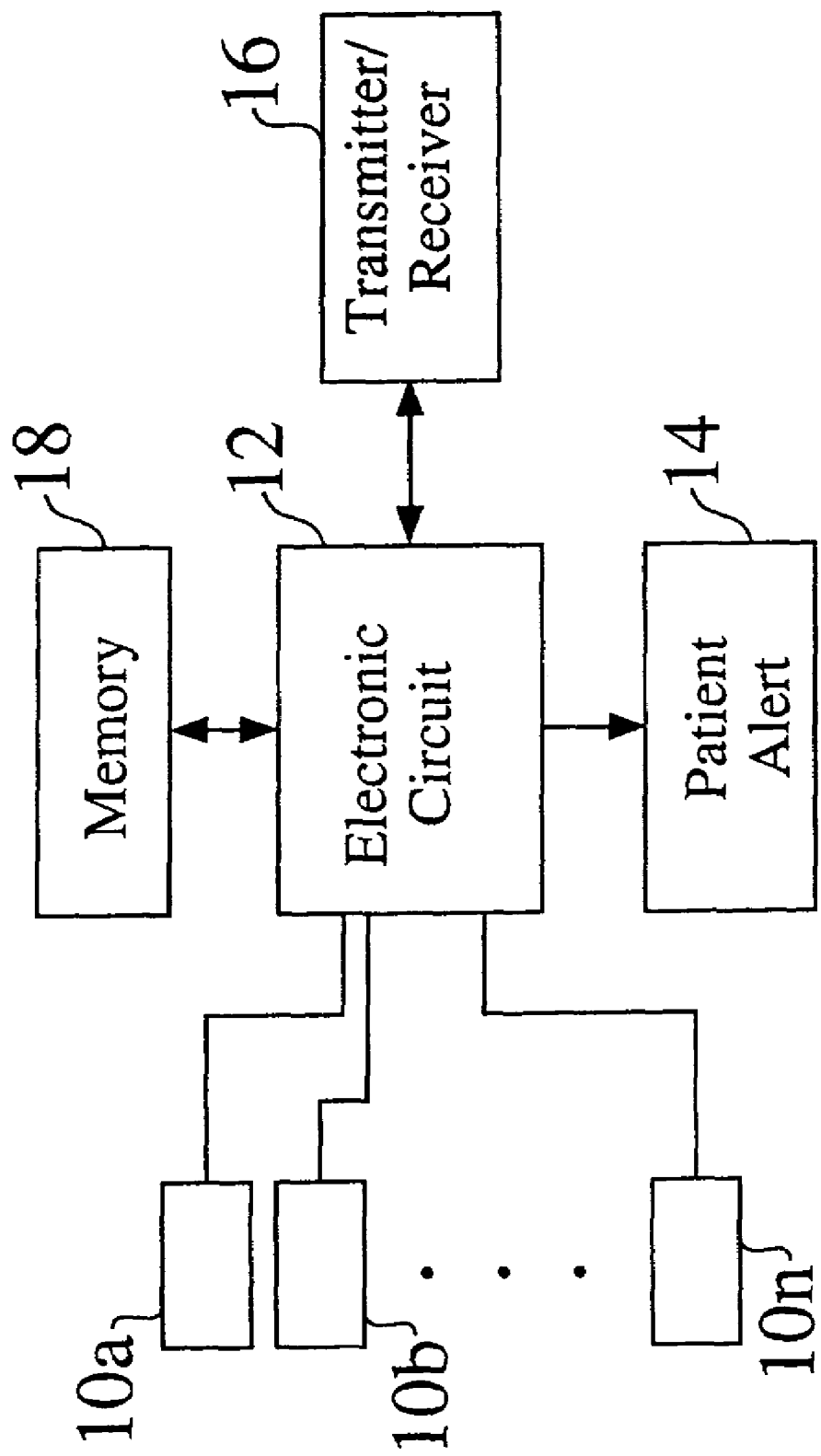
FIG. 1 shows a functional block diagram of an embodiment of the invention.

A functional block diagram of a monitor according to an embodiment of the present invention is shown in FIG. 1. One or a plurality of sensors 10a, 10b, ... 10n is connected to an electronic circuit 12, which in turn is connected to a patient alert 14, transmitter/receiver 16, and memory 18, with each of elements 14, 16 and 18 being optional. In an embodiment, the electronic circuit 12 includes a low-power microprocessor. In alternate embodiments the microprocessor is excluded, or control and higher level processing is performed by a microcontroller, an embedded system, a programmable logic device such as a field-programmable logic array, or a combinatorial implementation of a state machine. In an embodiment the transmitter/receiver 16 is an integrated radio frequency telemetry unit. Other embodiments of the transmitter/receiver are possible, including acoustic, optic, electrostatic, and magnetic. In yet another embodiment the receiver is simply a reed switch capable of sensing the presence of a strong magnet, so that the device can be turned on and off externally, but lacks post-manufacturing programmability. In still other embodiments the patient alert and transmitter/receiver might not be included, so that the device lacks the ability to receive or transmit information. Such a device, by design, may be intended not to be capable of downloading data it has acquired or informing the patient of a change in status. Rather, it may be intended to be explanted in order for the stored data to be accessed. In another embodiment, the monitor lacks a receiver and is intended to run continuously in the same mode from the time of implant, i.e., it lacks programmability.

The patient alert provides notification to the patient. A variety of embodiments are possible, including acoustic, mechanical vibration, optic, thermal, and electrical stimulation. In an embodiment the patient alert is an inductive coil and magnetic which generates both sound and mechanical vibration. In an alternative embodiment, the patient alert function is incorporated into the electronic circuit 12 and transmitter/receiver 16.

Figure 2A:
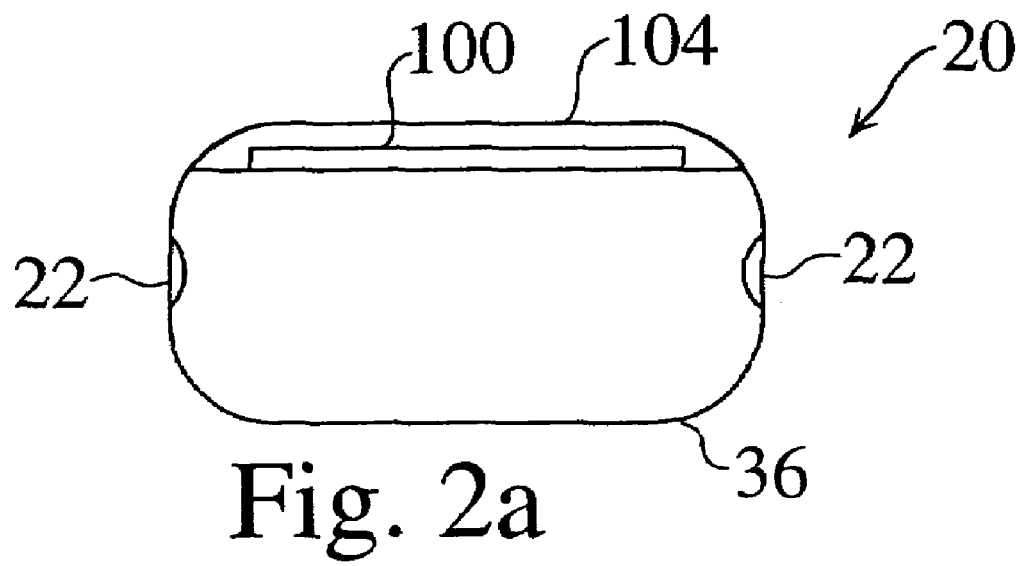
FIGS. 2a–2c provide various views of an embodiment of the invention.
Figure 2B:
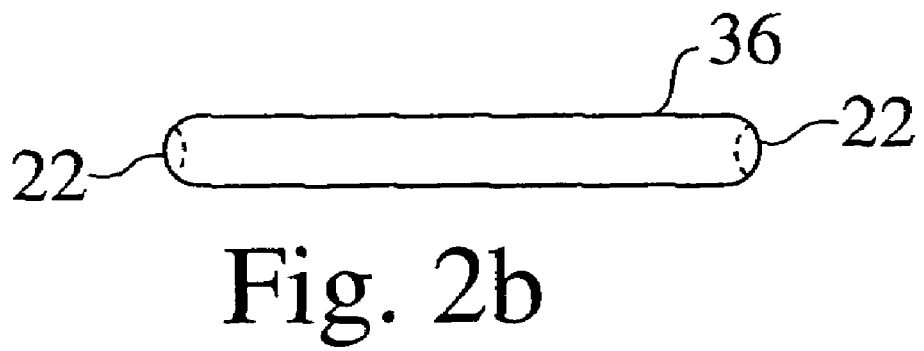
Figure 2C:
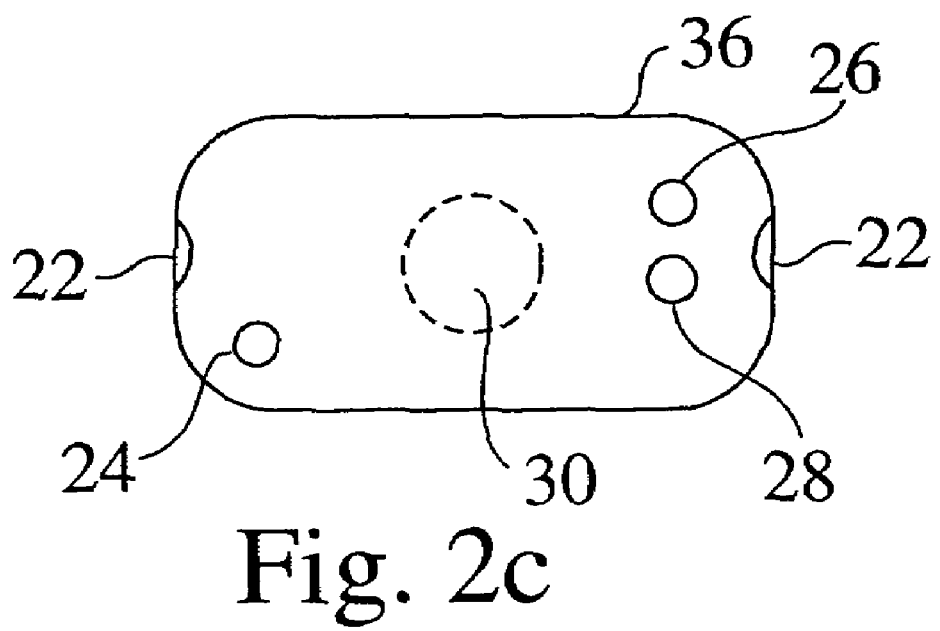
Figure 3A:
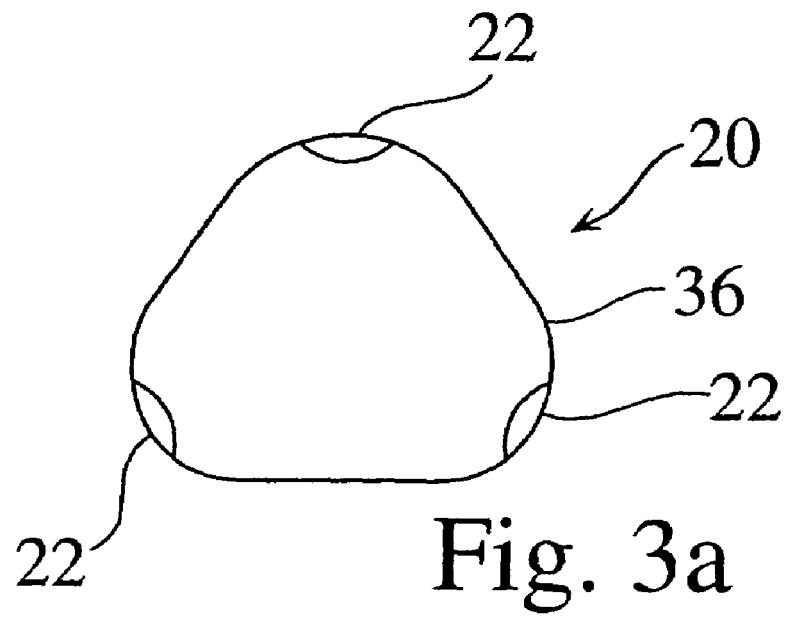
FIGS. 3a–3c provide various views of an alternate embodiment of the invention.
Figure 3B:
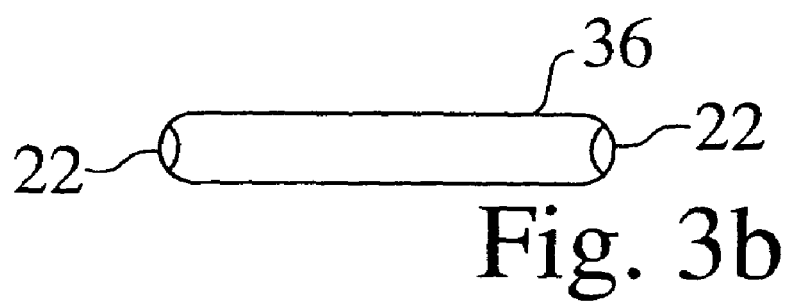
Figure 3C:
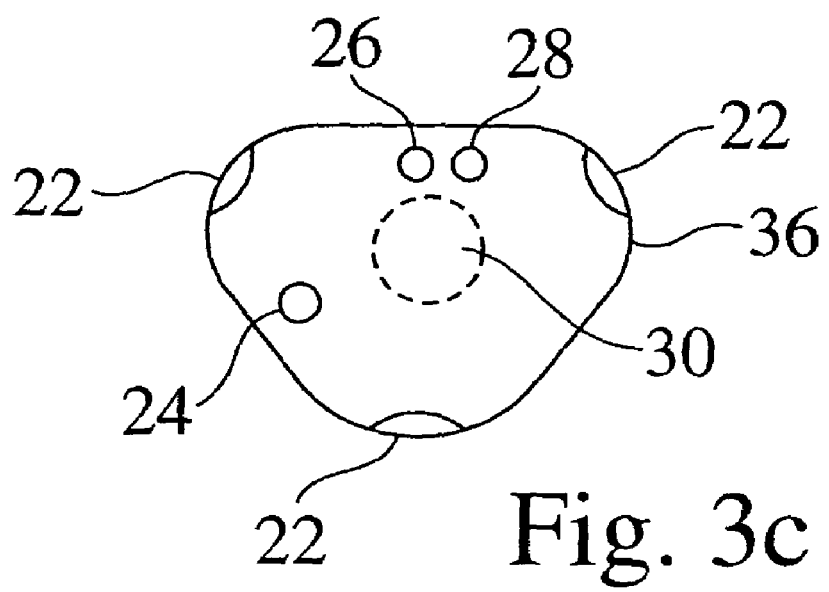

An external view of the monitor 20 is illustrated in FIGS. 2 and 3. In the embodiment shown in FIGS. 2a–2c, the device is small, thin, and oblong, with smooth surfaces and a physiologic contour which minimizes tissue trauma and inflammation. The oblong geometry of the monitor housing 36 is desirable because it maximizes separation of electrodes 22 and prevents rotation of the monitor within the tissue pocket, thereby allowing interpretation of the QRS morphology in an ECG sensed using electrodes 22. An antenna 100, mechanically stabilized and electrically insulated by an epoxy encasement 104, facilitates radio frequency telemetry. Two ECG electrodes 22 are present in an embodiment, one at each end of the oval formed by the monitor housing 36. In the alternate embodiment illustrated in FIGS. 3a–3c, three ECG electrodes 22 are present, one at each apex of the triangle formed by the device housing 36. These three electrodes allow the three standard surface ECG leads I–III to be approximated. In another embodiment, four or more ECG electrodes might be used, with each orthogonal electrode pair providing orthogonal ECG signals. Alternatively, an embodiment lacking ECG electrodes is possible. A further alternative has a single ECG electrode with the monitor housing acting as the other electrode in the pair. In addition to the ECG electrodes, a working electrode 24 of an electrochemical sensor is also shown in FIGS. 2 and 3, such as that previously described in the art in U.S. Pat. No. 4,853,091, which is incorporated herein by reference. In an embodiment this is specific for $O_2$ partial pressure, but other embodiments measure the concentrations or partial pressures of other metabolic gases or products, such as $CO_2$, pH, and lactic acid.

A light source 26 and detector 28, preferably LEDs and photodiode, respectively, are shown in FIG. 2c and FIG. 3c. In an embodiment a single source and a single detector are used for both vascular plethysmography and for measuring the oxygen saturation of arterial hemoglobin. The source is capable of independently generating two discrete wavelengths of light, preferably at 660 and 940 nm, in a way well known to those skilled in the art. The source and detector are preferably placed on the side of the device that, following implantation, faces the chest wall, and are configured such that light cannot pass directly from the source to the detector. The placement on the side of the device that faces the chest wall maximizes the signal to noise ratio by 1) directing the signal toward the highly vascularized musculature and 2) shielding the source and detector from ambient light that enters the body through the skin. Alternatively, at the risk of increasing susceptibility to ambient light, the optical source and sensor can be placed on the face of the device that faces the skin of the patient. In this configuration it can be used to provide high-speed optical telemetry.

The location of a microphone diaphragm 30 is indicated by the dotted line in FIGS. 2c and 3c. It is preferably placed such that it is directed toward the heart and lungs.

The embodiment of the sound sensor, which can be implemented using a microphone, accelerometer, or pressure transducer, is illustrated in FIG. 4. An embodiment is shown in FIG. 4a, in which the cross section of the monitor housing 36 is shown. A mechanical to electrical transducer 38 is directly affixed to the inside of the housing 36, and the acoustic properties of the housing 36 are such that the transducer successfully registers cardiac and pulmonary sounds. In particular, the resonant frequency of the housing 36 is outside the frequency range of interest, 5–300 Hz for heart sounds and 500–3000 Hz for pulmonary rales. In addition, no vibrational nodes occur at the site of the transducer for the frequency range of interest. This embodiment is desirable because no additional manufacturing steps are required in the production of the monitor housing 36. In addition to the ease of manufacturing that this embodiment offers, it is desirable because the preferred thickness of the diaphragm is 0.005–0.015 inches, which is the typical wall thickness used in conventional implantable devices such as pacemakers and defibrillators.

The mechanical to electrical transducer 38, preferably a piezoelectric element such as that provided by MSI (Measurement Specialties, Inc, Sensor Products Division, Folsom, Calif.), is attached at the middle of face of the monitor housing 36. A pair of leads 40 of the transducer 38 are connected to the inputs of a signal conditioning circuit (not shown), which is contained in the electronic circuit 12 shown in FIG. 1. The signal conditioning, filtering, and amplification appropriate for a piezoelectric sound transducer is well known in the field of sensors, and is therefore not presented here.

Figure 4A:
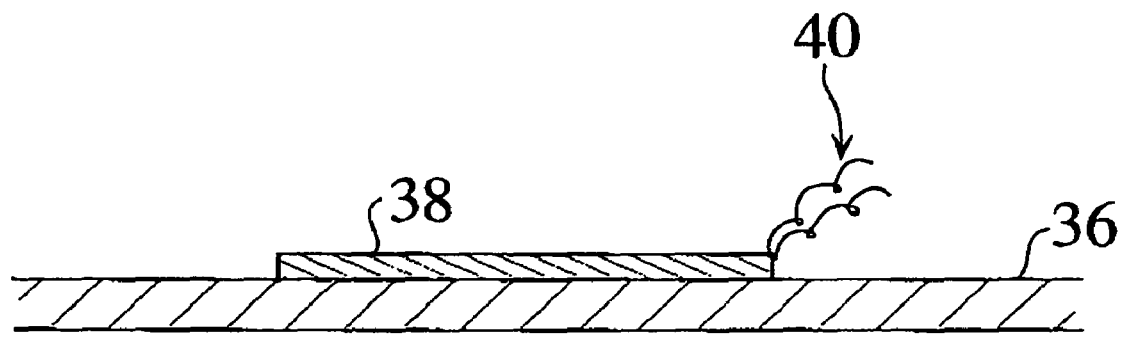
FIGS. 4a–4e show top sectional views of a sensor portion of the housing for various embodiments illustrating the microphone sensor.
Figure 4B:
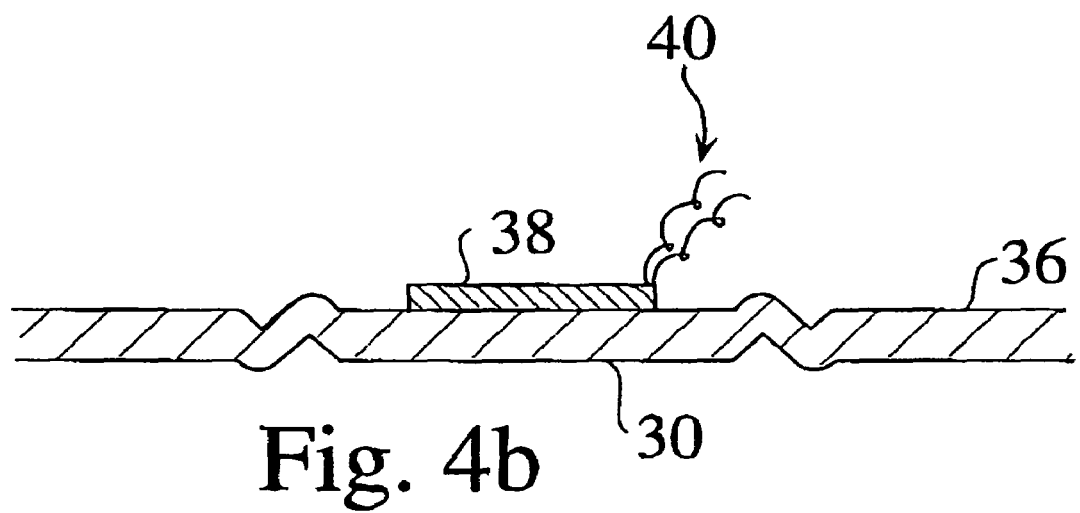

An alternate embodiment of the sound sensor establishes a mechanically well defined acoustic diaphragm 30 during the forming of the monitor housing 36, as illustrated in FIG. 4b. In order to avoid the need for additional manufacturing steps, the diaphragm 30 is created during the same manufacturing step in which the device housing 36 is formed. This is achieved by including concentric ridges and grooves in the die such that the illustrated pattern results. The resulting ridges and groves in the formed device housing 36 produce a well-defined diaphragm 30 that vibrates according to the pressure wave of the incident sound, with greatest amplitude of oscillation at the diaphragm center. In an alternate manufacturing process, the ridges and grooves which define the diaphragm can be formed, coined, or machined in a separate step after the housing is formed or produced. Other arrangements of groves and ridges are possible. In an alternate embodiment, no grove is produced on the exterior of the housing. While this compromises the mechanical definition of the diaphragm, it provides a smooth exterior surface which minimizes the risk of infection.

Figure 4C:
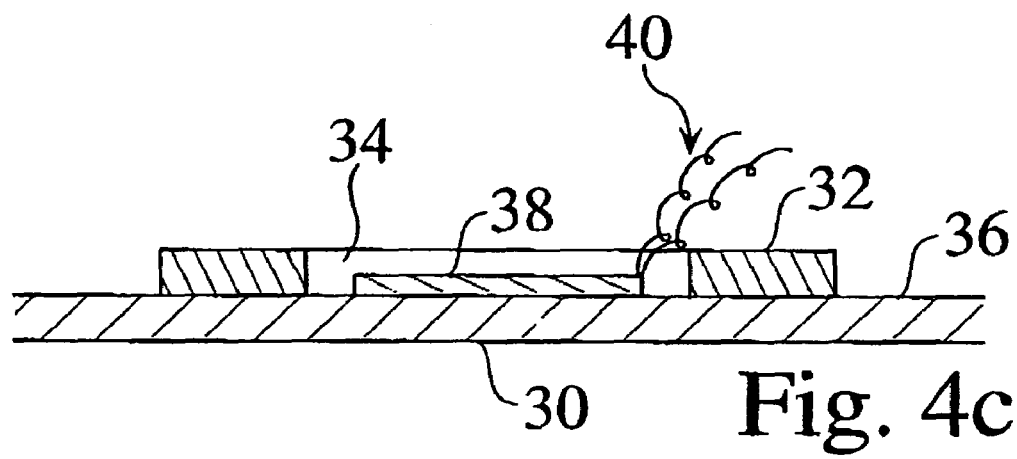

In another alternate embodiment illustrated in FIG. 4c, an annular disk or plate 32 with a circular hole 34 is attached to the inside of the monitor housing 36 using a laser weld, a resistance weld, glue, epoxy, or some other suitable attachment means. The annular disk or plate 32 can be a functional component of the monitor, such as a battery, capacitor, or circuit board. Because of the encircling rigid and relatively more massive annular disk or plate 32, the portion of monitor housing 36 that is exposed through the circular hole 34 is a mechanically well-defined diaphragm 30. When sound strikes the device housing 36, the diaphragm 30 moves according to the pressure wave of the sound, with the greatest movement amplitude occurring at the center of the diaphragm. Depending on the properties of the housing, a complete annulus might not be necessary. Rather, curved or linear segments of supporting material attached to the inside of the device housing might adequately reduce the area of the diaphragm so that its resonant frequency is sufficiently high and no vibrational nodes are produced at the site of the mechanical to electrical transducer.

Figure 4D:
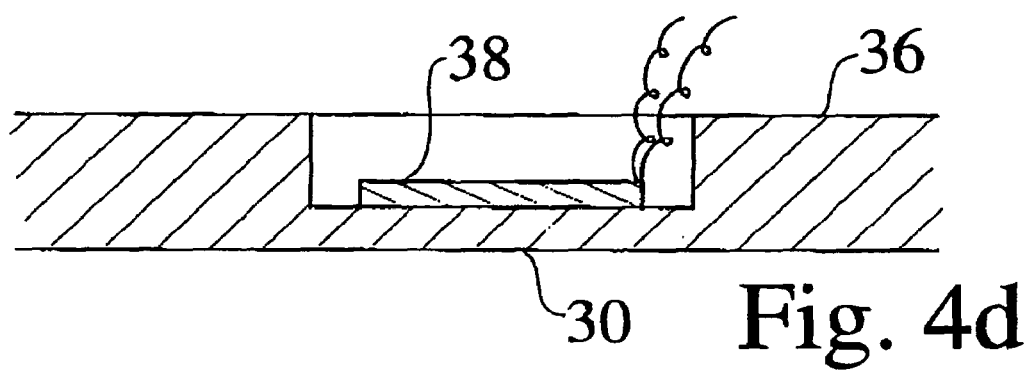

FIG. 4d shows an alternate embodiment of the sound sensor. Here the device housing 36 is formed, stamped, or machined such that the diaphragm thickness, typically 0.005 inches, is less than the thickness of the surrounding housing. This provides a mechanically well-defined diaphragm 30 which, when sound strikes the device, undergoes the largest amplitude deflection at its center. Transducer 38 is used to sense vibrational motion of diaphragm 30.

Figure 4E:
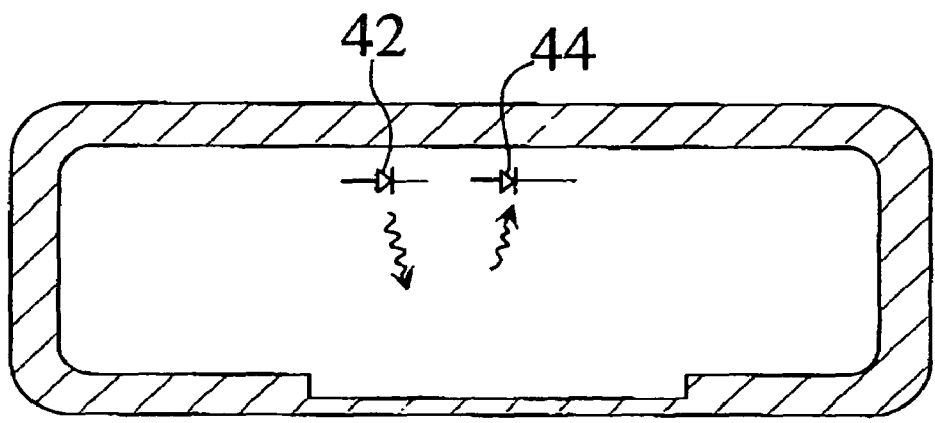

FIG. 4e shows an alternate embodiment of the mechanical-to-electrical transducer, in which a laser diode 42 and photodetector 44, such as a phototransistor, photodiode, piezoelectric, or thermoelectric material such as PVDF, are configured so that transduction is performed by laser interferometery. The technology of focusing elements and related circuitry, not shown, are well developed in the art of interferometery, as discussed in the book "Handbook of Modern Sensors," by Jacob Fraden.

Figure 5A:
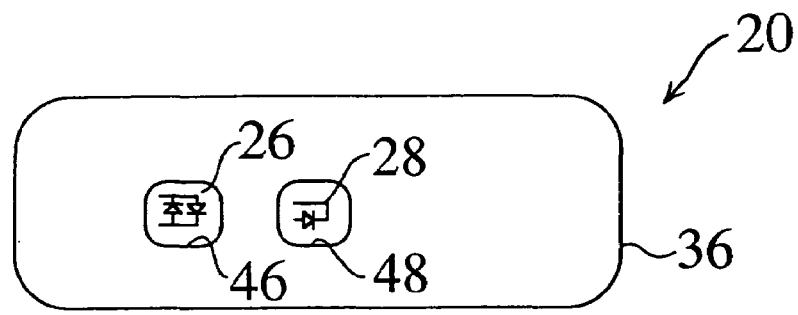
FIGS. 5a–5d show plan and sectional views illustrating the oxygen saturation and vascular plethysmography sensor.

FIG. 5a shows an exemplary combined $O_2$ saturation and vascular plethysmography sensor of the monitor 20. In FIG. 5a, the light source 26, preferably parallel and oppositely oriented red and infrared LEDs, are positioned such that light is directed into the overlying tissue, and the light detector 28, preferably a photodiode, is positioned such that it collects light reflected by the overlying tissue. The electronic circuitry associated with the light source and sensor is well known for external pulse oximeters, and is described in, e.g., U.S. Pat. Nos. 4,869,254 and 5,078,136, incorporated herein by reference. Tailoring the known art for novel use in an implantable, reflective configuration is straightforward. In alternate embodiments, the plethysmography sensor or the $O_2$ saturation sensor, or both, might not be used in the monitor. Alternate embodiments of the plethysmography sensor use a single wavelength of light, or a broad spectrum of many wavelengths. In the alternate embodiments, the light source can be any source of radiant energy, including laserdiode, heated filament, and ultrasound transducer. The detector can be any detector of radiant energy, including phototransistor, photodetector, ultrasound transducer, piezoelectric material, and thermoelectric material. In still other alternate embodiments vascular plethysmography is performed with non-radiant methods, including mechanical strain, electrical impedance, and pressure. Alternate embodiments of the O2 saturation sensor might use more than two wavelengths. Alternatively, a single wavelength driven at two different current levels might be used, such as in the technique described by Cohen et al. in U.S. Pat. No. 4,815,469, which is incorporated herein by reference.

As with most of the sensors described here, the vascular plethysmography and arterial $O_2$ saturation sensors can be used in noninvasive, external embodiments, in contrast to incorporation in an implantantable monitor. These optical sensors are particularly attractive candidates for an external embodiment, since electrical contact with the skin or direct contact with subcutaneous tissue is not necessary, in contrast to, for example, ECG leads and chemical sensors, respectively. Furthermore, the sensors can be made small and can conveniently attach to a peripheral portion of the body, such as finger, toe, or ear, in contrast to, for example, a surface microphone, which is optimally position over the heart or great vessels. Thus, patients are likely to tolerate regular use of these sensors for an extended period of time, such as during sleep each night. Particular embodiments include a finger cuff, a wristband, a configuration resembling a watch, and a configuration resembling a clip-on earring. The sensor could be tethered to a larger unit containing the bulk of the electronic circuitry. In this case, the monitor would be worn primarily when the patient is sleeping. Alternatively, the raw data from the sensors could be continuously telemetered to a larger processor, which might be worn on the patient's clothing or located in the patient's home. In this case, the monitor could be worn both during sleep and during activity. Nevertheless, despite the cost advantages of an external embodiment, such an approach necessarily requires patient cooperation. Because of the disadvantages associated with this, as described above in Discussion of the Prior Art, the preferred embodiment for these sensors is in an implanted, extravascular configuration.

Figure 5B:
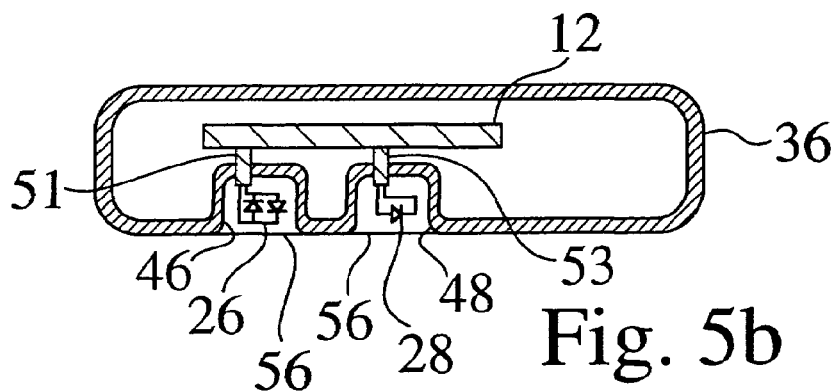
Figure 5C:
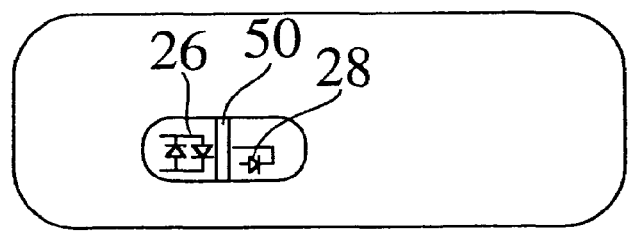
Figure 5D:
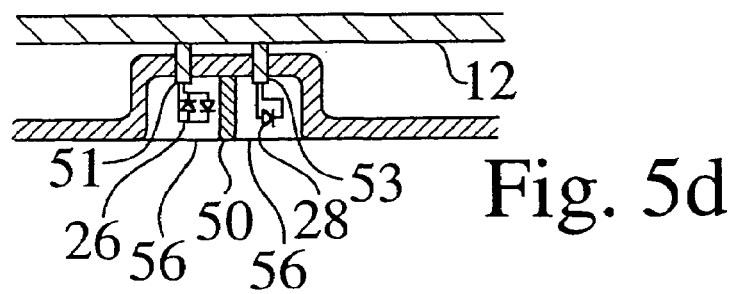

Returning to the embodiment of the combined vascular plethysmography and $O_2$ saturation sensor shown in FIG. 5a, the source 26 and detector 28 are placed in separate wells, 46 and 48, respectively, that are created when the monitor housing 36 is machined, formed, or cast. In an embodiment, each well 46 and 48 is formed using the minimum volume necessary to contain its feed-through connector and optical device. Locating the source and detector in separate wells ensures that no light passes directly between them. In the alternate embodiment shown in FIGS. 5c and 5d, source 26 and detector 28 are placed in the same well with an opaque barrier 50 placed between them. Returning to the embodiment of FIGS. 5a and 5b, the source and the detector are physically positioned within the wells 46 and 48, respectively, such that the amount of light received at the detector is maximized. In particular, they are angled toward each other such that the directions of greatest optical power and sensitivity are aligned. Furthermore, in accordance with an embodiment the optical devices have inherent directionality to avoid the need for lenses or other focusing elements, though these are used in alternate embodiments. The remaining space in the well is filled with epoxy 56 such that the surface of the monitor 20 is smooth and flat, thereby minimizing the risk of tissue trauma and infection. The optical source 26 and detector 28 are connected via feed-through connections 51, 52, respectively, to the electronic circuit 12, thus ensuring hermeticity. Placing the optical components 26 and 28 in wells 46 and 48 thus enhances optical isolation while maintaining hermeticity, in contrast to the prior art, which risked the integrity of the hermetic seal by using a transparent window, or sacrificed optical isolation and therefore performance of the sensor, by placing the optical components together in a header. Furthermore, the solution of the present invention is applicable to both devices with headers and those without.

Figure 5E:
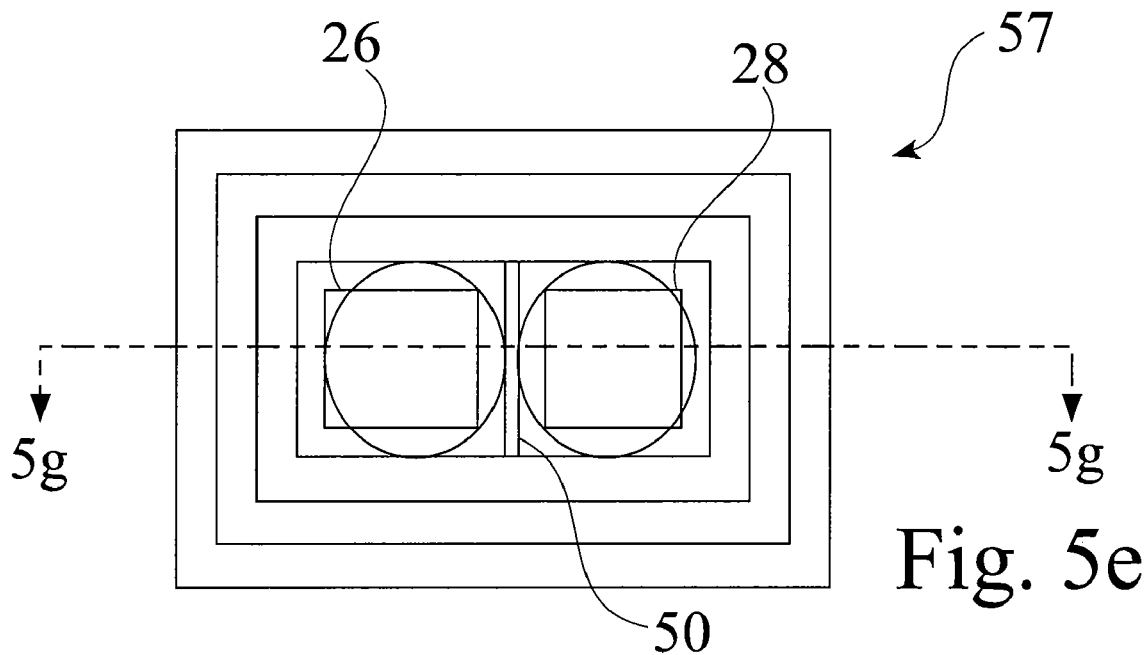
FIGS. 5e–5g show plan, side and sectional views of another embodiment of an oxygen saturation and vascular plethysmography sensor.
Figure 5F:
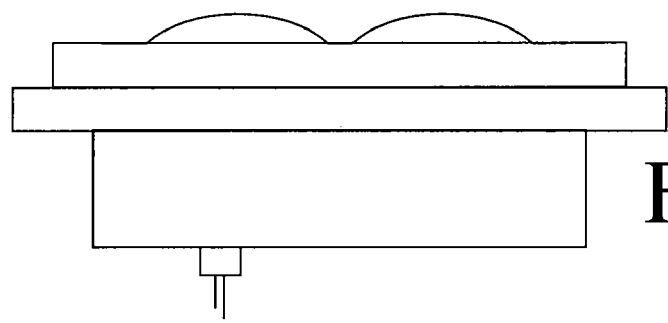
Figure 5G:
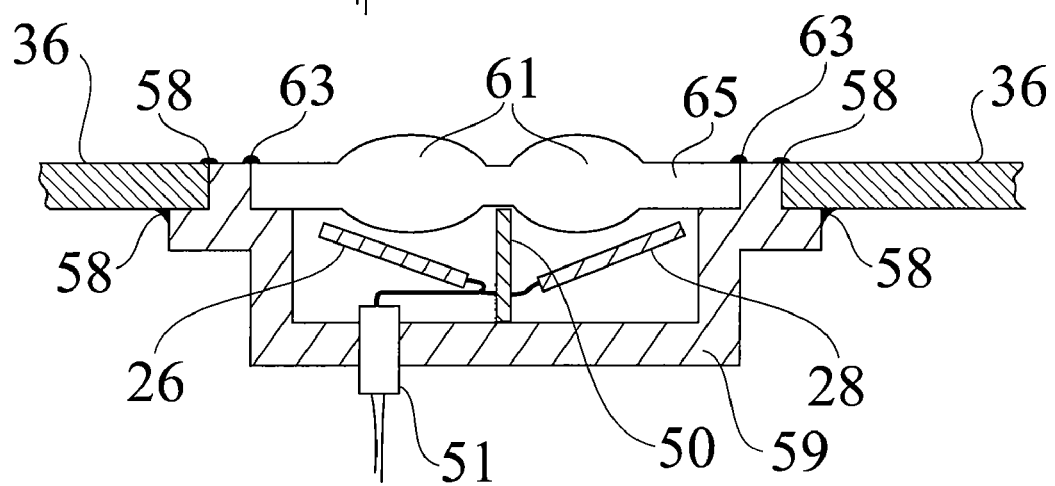

FIGS. 5e–5g show a further embodiment of a combined $O_2$ saturation and vascular plethysmography sensor of the monitor 20. In this embodiment, the light source 26, preferably parallel and oppositely oriented red and infrared LEDs, is positioned such that light is directed into the overlying tissue, and the light detector 28, preferably a photodiode, is positioned such that it collects light backscattered and reflected by the overlying tissue. The photoelectric components are placed in a sensor module 57 which is assembled separately from the host device, for example a monitor, pacemaker, or ICD. FIGS. 5e and 5f show two views of the intact sensor module. FIG. 5g shows the sensor module 57 in cross-section and integrated into the housing 36 of the implantable device. After assembly the sensor module 57 is laser-welded to the housing of the implantable device. The laser weld 58 provides a hermetic seal between the external environment and the interior of the implantable device, thus isolating the two spaces. In the preferred embodiment the space surrounding the optoelectronic components is potted with clear, biocompatible epoxy. A transparent covering 65 is placed over the photoelectric components and hermetically sealed with a gold braze and laser weld 63 to the titanium structure 59 of the sensor module 57. Such transparent coverings and processes for hermetic sealing are known in the art, such as synthetic sapphire products marketed by Imetra, Inc (Elmsford, N.Y.) and gold brazing performed by Wilson Greatbatch Technologies, Inc (Clarence, N.Y.). In the preferred embodiment the transparent covering 65 includes simple lenses 61 to focus and direct the transmitted and backscattered light. A feed-through connector 51 passes conductors from the interior of the implanted device to the optoelectronic components 26 and 28 within the sensor module. The feed-through connector 51 is laser welded to the sensor module structure 59 thus providing a hermetic separation between the interior of the sensor module and the interior of the implanted device. The optical barrier of 50 prevents direct transmission of light from the source 26 to the detector 28.

In alternate embodiments the transparent covering 65 does not incorporate optical focusing elements. In other embodiments, a transparent covering is not used. Rather, the interior of the sensor module is filled with transparent, biocompatible epoxy potting, which separates and electrically insulates the optoelectronic components from the overlying tissue. In accordance with an embodiment, the sensor module structure 59 is machined or formed from a single piece of titanium. The optoelectronic components 26 and 28, feed-through connector 51, and optical barrier 50 are placed within the sensor module prior to placement and hermetic sealing of the transparent covering 65. In alternate embodiments the sensor module structure is composed of two pieces which allows placement of the transparent covering 65 and sealing of both sides of it prior to placement of the photoelectric and other components. FIGS. 5e–5f illustrate a rectangular sensor module 57, however a circular design can be used as well, which may minimize stress concentration and facilitate manufacturing.

In still other embodiments, the plethysmography sensor or the $O_2$ saturation sensor, or both, might not be used in the monitor. Alternate embodiments of the plethysmography sensor use a single wavelength of light, or a broad spectrum of many wavelengths. In the alternate embodiments, the light source can be any source of radiant energy, including laserdiode, heated filament, and ultrasound transducer. The detector can be any detector of radiant energy, including phototransistor, photodetector, ultrasound transducer, piezoelectric material, and thermoelectric material. In still other alternate embodiments vascular plethysmography is performed with non-radiant methods, including mechanical strain, electrical impedance, and pressure. Alternate embodiments of the $O_2$ saturation sensor might use more than two wavelengths. Alternatively, a single wavelength driven at two different current levels might be used, such as in the technique described by Cohen et al. in U.S. Pat. No. 4,815,469, which is incorporated herein by reference.

Figure 6:
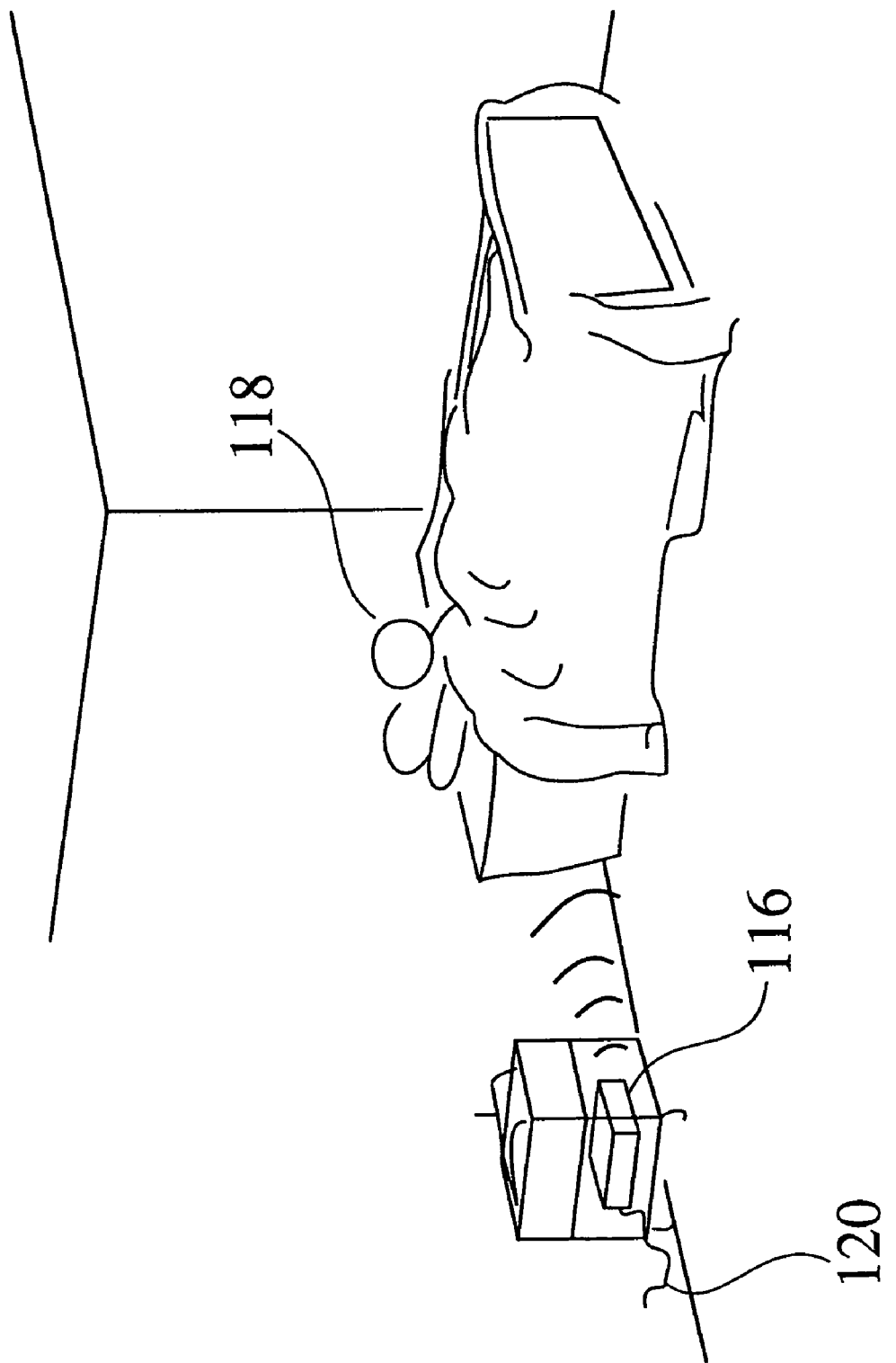
FIG. 6 illustrates the use of the telemetry-at-a-distance feature of an embodiment of the invention.

FIG. 6 illustrates the placement of the external telemetry unit 116 in the patient's bedroom, which, using telemetry at a distance, allows the transfer of data to and from the implanted device, without the active participation of the patient 118 or clinician. This is in contrast to the current art, which requires both the cooperation of the patient and the active participation of a health care provider. For example, in U.S. Pat. No. 5,342,408, incorporated herein by reference, a signal strength indicator is provided with allows the health care provider to optimally position the external telemetry antenna. In an embodiment of the present invention, the external telemetry unit 116 is positioned in a location regularly frequented by the patient, such as the patient's bedroom, and is preferably connected to the telephone line 120, allowing transfer of data to a central location for further processing or review by a clinician.

Telemetry is preferably implemented in the implantable monitor using the TR1000, a single-chip, low-power, 916.5 MHz transceiver manufactured by RF Monolithics, Dallas, Tex. The operating frequency of 916.5 MHz is preferred because of the modest requirements on antenna size it imposes; a standard ¼ wavelength whip antenna for this frequency is just 8 cm long. The implanted nature of the monitor, however, precludes the use of a simple whip antenna. Furthermore, omnidirectional antenna gain, an advantage not offered by the whip antenna, is desirable since the relative orientation of the implanted monitor and external telemetry unit is not know a priori and cannot be controlled, in contrast to the present state of the art, in which a clinician manually maneuvers the external antenna in order to optimize the signal strength. These considerations lead to the embodiment of the antenna for the implantable monitor shown in FIG. 7a. The antenna 100 passes through the housing 36 of the monitor 20 via a feed-through connection 102, thus maintaining hermeticity. An insulating stabilizer 104 such as epoxy provides mechanical protection of the antenna 100 and electrically insulates it both from the overlying tissue and from the monitor housing 36, which acts as the antenna ground plane. This arrangement thus approximates the well-known stub antenna configuration. The antenna 100 is ideally 5 cm long. Referring now to FIG. 7b, which is a cross-sectional view of monitor 20 along lines 7b–7b, a transceiver 108 is grounded to the monitor housing 36, thereby establishing the ground plane. An optional tuning inductor 106 is placed between the transceiver 108 and the antenna 100, which compensates for the impedance loading effects of tissue and internal components of the monitor (not shown). The inductor is preferably adjusted so that the impedance seen by transceiver 108 is 50 ohms.

An alternate embodiment of the antenna is shown in FIG. 7c, where the antenna 100 is a flexible lead extending from a header 110 of the monitor 20. Alternatively, and in contrast to the header 110 which allows post-manufacturing attachment of the antenna 100, the base of the antenna 100 can be permanently secured with epoxy or other material to the monitor housing 36 during manufacture, a simpler and less expensive process than that required to form a functional header.

Yet another alternate embodiment of the antenna is shown in FIGS. 7d and cross-sectional view 7e, where the antenna 100 is implemented using the well-known slotted plane configuration. Dotted lines indicate the locations of the positive 102 and ground 103 feed-through connections of the transceiver 108. An insulator 104, preferably epoxy, mechanically stabilizes and electrically insulates the antenna 100 from the housing 36 of the monitor 20 and the overlying tissue.

Still another alternate embodiment integrates the antenna 100 and ground plane 112 into the printed circuit board 114 used by the circuitry of the monitor, as shown in FIG. 7f. The antenna is thus placed entirely within the housing of the monitor. While internal placement of the antenna 100 will attenuate the signal transmitted from and received by the monitor, in some applications the reduced manufacturing costs may warrant this approach. The transceiver 108 is placed at the intersection of the antenna 100 and ground plane 112, and is connected to both.

In yet another embodiment the antenna is wrapped around the periphery of the monitor housing and insulated and secured in an epoxy encasement.

The implantable hemodynamic monitor is configured for subcutaneous or submuscular implantation. In accordance with an embodiment, the routine operation of the monitor does not require patient participation or cooperation to monitor the patient's condition. The monitor automatically analyzes the data it acquires, recognizes a worsening of disease status, and notifies the patient of the need for physician consultation. As illustrated in FIG. 6, an external telemetry unit 116 can be available in the patient's home. When the implanted monitor recognizes worsening disease status, the patient is notified, and data is telemetered via the external telemetry unit 116 and via the telephone lines 120 to the physician or to a central location for further review.

In another embodiment the external home telemetry unit is not available. In this case when the patient is notified by way of an audible or vibrational warning signal from the monitor of potentially worsening disease status the patient should consult with a physician in person or over the telephone.

In yet another embodiment data is routinely and automatically conveyed to the external telemetry unit 116 which performs more computationally intensive analysis or delivers the data via telephone lines 120 to a central location for further analysis or review.

In still another embodiment, the patient may be required to actively participate in the routine telemetry of data to the external telemetry unit 116 or a central location, but would preferably not be required to actively participate in the data acquisition, thereby avoiding the disadvantages of noninvasive monitors as described above in Discussion of the Prior Art.

In an additional embodiment, data obtained from the sensors is combined with the patient's responses to questions concerning the patient's subjective condition, habits, or behavior posed by the external unit.

The electronic circuit shown in the functional block diagram of FIG. 1 provides the high level processing of the monitor. The preferred and alternative embodiments of the electronic circuit are now described. The implementation of the embodiments will be obvious to one skilled in the art, and will therefore not be presented in detail. The processing of data generated by the individual sensors will be described in detail below.

In accordance with an embodiment, the electronic circuit does not acquire and process data continuously. Rather, the electronic circuit contains a timer that periodically initiates data acquisition. In an embodiment, one of the sensors is an accelerometer. The output of the accelerometer is used by the electronic circuit to condition data acquisition on the activity of the patient. Specifically, data is scheduled to be acquired and processed at one-hour intervals. Data is acquired at the scheduled time if the patient has been at rest for a predetermined period, preferably at least 10 minutes. If the rest condition is not satisfied then data is acquired the next time the condition is satisfied.

There are a variety of levels of information that the electronic circuit can extract from the collection of sensors. For example, the electronic circuit may simply store raw data for later retrieval and analysis by a physician. In this embodiment, the device functions primarily as a tool that allows the physician to optimize medical therapy or work up a possible exacerbation. Alternatively, the raw data might be stored over an extended but relatively short period of time, such as 24 hours, and periodically and routinely conveyed by means of the transmitter to an external module which performs high level diagnostic analysis or data archiving. In yet another embodiment, the electronic circuit includes a microprocessor used to derive a high-level clinical diagnosis from the collection of sensor outputs. For example, the electronic circuit might deduce that an acute heart failure exacerbation is developing and that the patient and physician should be notified. In this case the device would activate the patient alert 14 shown in FIG. 1 to inform the patient that medical attention should be sought. In accordance with an embodiment, the alert is provided through an electromechanical transducer that generates sound and mechanical vibration, which instructs the patient to telemeter data from the implanted hemodynamic monitor to the physician or emergency room. The physician can then review the data, interview the patient, and determine what course of action is appropriate. In accordance with an embodiment, the electronic circuit assesses whether an exacerbation is developing by comparing the contents of an alert counter to a predetermined threshold, programmed by the physician or manufacturer. The alert counter is incremented for each measure calculated by the electronic circuit that suggests an exacerbation is developing. In accordance with an embodiment, each measure is equally weighted, but in other embodiments more sensitive and specific measures may be weighted more heavily than less sensitive and specific measures. In other embodiments an arithmetic combination of the measures is compared to a predetermined threshold.

Turning now to the preferred and alternate embodiments of specific sensors and the processing of their respective outputs by the electronic circuit, the general observation is made that the electronic circuit can provide processing at a variety of levels, depending on the sensor involved and the embodiment of the electronic circuit. Consider the case in which the sensor is an ECG electrode pair. The electronic circuit may simply sample the sensor output and digitally store the waveform for later review by a physician. In this way the physician can examine the raw data for the development of ST segment depressions or other morphology abnormalities, which are well known to clinicians, that suggest acute heart failure or ischemia. Alternatively, the device may itself analyze the data for the development of morphology abnormalities that suggest acute heart failure or ischemia. In another embodiment, the circuit may extract and store higher level information, such as the RR interval. In this way morphology information is lost but beat-to-beat rate information is retained. A further alternative is that the circuit may analyze the beat-to-beat rate information to extract a measure of sympathetic/parasympathetic balance, such as the ratio of low frequency to high frequency variability, a measure that is well known in the art. See, for example, the book "Heart Rate Variability," by Malik, M., and Camm, A. J., Eds, Futura Publishing Company, Inc, 1995, the disclosure of which is incorporated herein by reference. Thus, there is a hierarchy of abstraction that the electronic circuit might perform on the output of each sensor.

Two ECG electrodes 22 are used in an embodiment, one at each end of the housing 36 of the monitor 20, as illustrated in FIG. 2. An ECG signal is derived from these two electrodes, in a way well-known to those skilled in the art. See, for example, "Medical Instrumentation," by J. G. Webster, John Wiley and Sons, Inc, 1998.

Figure 8:
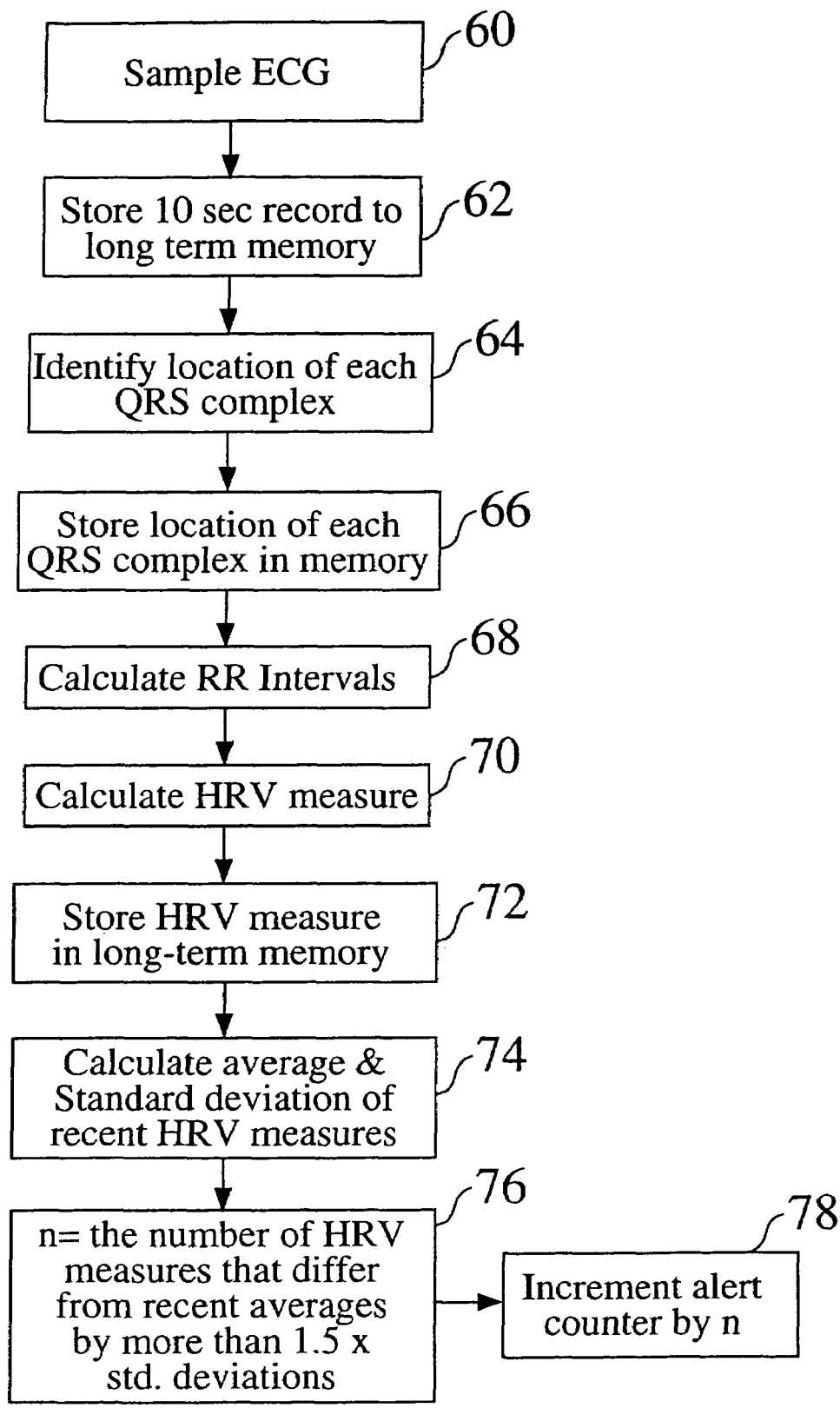
FIG. 8 is a flowchart which describes the processing performed by the electronic circuit on the output of the ECG sensors.

In an embodiment the electronic circuit 12 shown in FIG. 1 processes the output of the ECG electrodes as illustrated in the flow chart of FIG. 8. First, in step 60, the ECG data is continuously sampled, preferably at 500 Hz for 5 minutes. Then, a short segment of the raw data, preferably 10 seconds in length, is stored at step 62 in long-term storage for later retrieval, thus allowing the physician to review the morphology for signs of ischemia. Next, the location of each QRS complex is identified in step 64 and stored in step 66 in memory for later use in the analysis of other sensor outputs. The intervals between QRS complexes are derived at step 68. From this data series, measures of heart rate variability (HRV) are derived at step 70, preferably the standard deviation of RR intervals, and the ratio of low to high frequency power, using methods well known to those skilled in the art. (See above referenced book by Malik, M., and Camm, A. J., Eds., and references contained therein.) An increase in sympathetic tone reflected in the HRV measures is consistent with a developing heart failure exacerbation. These HRV measures are then stored at step 72 in long-term memory for later retrieval and review by a physician. The electronic circuit computes the average and standard deviations of recent HRV measures at step 74, preferably using those obtained over the last 24 hours. The number of current HRV measures that differ from their respective recent average by more than 1.5 times their respective standard deviations is counted at step 76, and this sum is added to the alert counter contained in the electronic circuit at step 78.

In alternate embodiments of the invention the variability over specific frequency ranges is examined. In particular, the presence of respiratory fluctuations is tested by examining variability in the range 0.17 Hz to 0.4 Hz, and the presence of Mayer waves is tested by examining variability in the range 0.03 Hz to 0.1 Hz. The absence of fluctuations in these frequency bands suggests that disease status is worsening.

In another alternate embodiment HRV is based not on the intervals between cardiac contractions, but instead on the number of cardiac contractions occurring during predetermined counting intervals. Such an approach to HRV analysis is described in the article by Turcott and Teich entitled "Fractal Character of the Electrocardiogram: Distinguishing Heart-Failure and Normal Patients," 1996, *Ann. Biomed. Engr.*, 24:269–293, incorporated herein by reference.

HRV analysis ultimately requires the times of cardiac contractions or some other cardiac event or point in the cardiac cycle. In an embodiment these are obtained using the ECG electrodes 22 incorporated into the monitor housing 36, as shown in FIG. 2. Other embodiments of HRV analysis are based on nonelectrical techniques for determining the times of cardiac contractions. Examples of nonelectrical modalities include vascular plethysmography and heart sounds (described below), as well as ultrasound and pressure transduction. By transmitting an ultrasound signal from the housing of an implantable device or from the surface of the body, and by monitoring the reflected wave, ultrasound can be used to identify the locations in time of atrial or ventricular contractions. Alternatively, a lower power and higher frequency signal can be used to detect pulsations in the vasculature near the ultrasound transducer. Since these pulsations are generated from ventricular systole, they provide a marker of a particular point in the cardiac cycle, and can thus serve as the basis for HRV analysis. A pressure transducer placed extravascularly can similarly detect systolic pulsations in the nearby vasculature since during the pulsatation the expanding arteries and arterioles increase in volume and thereby increase the hydrostatic pressure of the interstitial fluid. A pressure transducer placed in an intracardiac location can obviously provide a robust indication of the times of cardiac contractions, but such a placement has several undesirable consequences as described above in Background of the Invention.

In an embodiment, the occurrence of the QRS complex represents the time of ventricular contractions. In alternate embodiments R waves, Q waves, T waves, and other individual components of the ECG are used to represent the time of contraction. In alternate embodiments based on the intracardiac electrogram, fiducial points in the signal are taken to represent the time of contraction, though these may not correspond in an obvious way to the waves and complexes of a standard surface ECG. In still other embodiments, the occurrence of a P wave or other marker of atrial activity is used as a fiducial point. Basing HRV analysis on the P wave has the advantage of more directly reflecting the autonomic modulation of the sinus node, since the effect of variable delay through the atrioventricular node is eliminated. However, P-wave detection or detection of other markers of atrial activity has the disadvantage of being more technically difficult.

Figure 9:
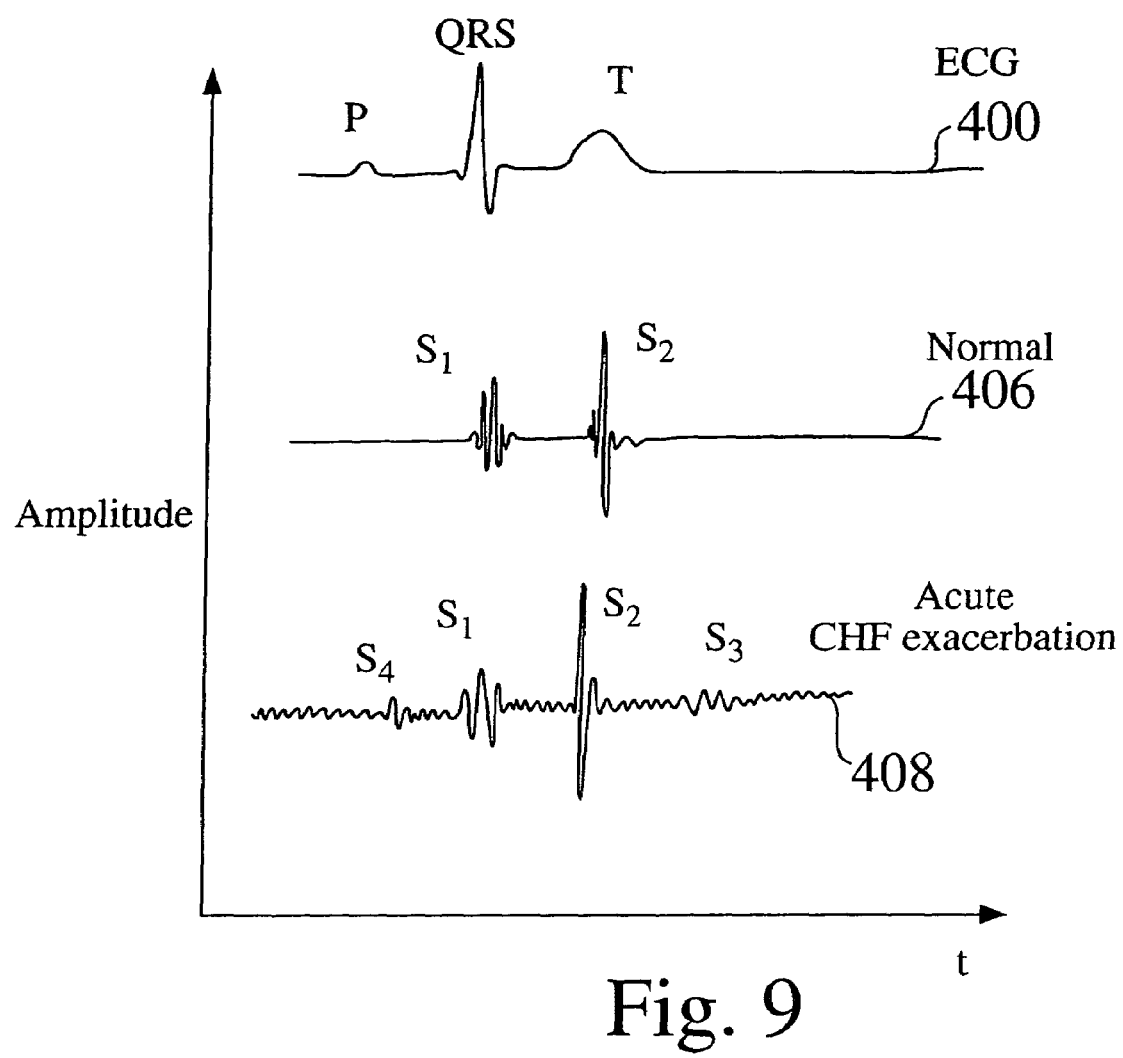
FIG. 9 illustrates a patient's ECG along with the phonocardiogram during a normal hemodynamic state and during an acute heart failure exacerbation.

FIG. 9 illustrates a phonocardiogram from the sound sensor with a patient in the normal state 406, and during a heart failure exacerbation 408. For timing reference the ECG 400 is also illustrated. As is well known to clinicians, extra heart sounds (S3, S4) or 'gallops,' develop during a heart failure exacerbation. Furthermore, the decreased cardiac contractility associated with an exacerbation decreases the force with which the tricuspid and mitral valves close, thereby decreasing the amplitude and energy of the S1 sound. In addition, the increased arterial blood pressure associated with an exacerbation increases the force with which the and aortic valve closes, thereby increasing the amplitude and energy of the S2 sound. Finally, the pulmonary rales, discussed below, of an acute heart failure exacerbation adds low amplitude, high frequency noise to the phonocardiogram. These changes can be seen in FIG. 9 by comparing the normal phonocardiogram 406 to that representing an acute heart failure exacerbation 408.

Figure 10:
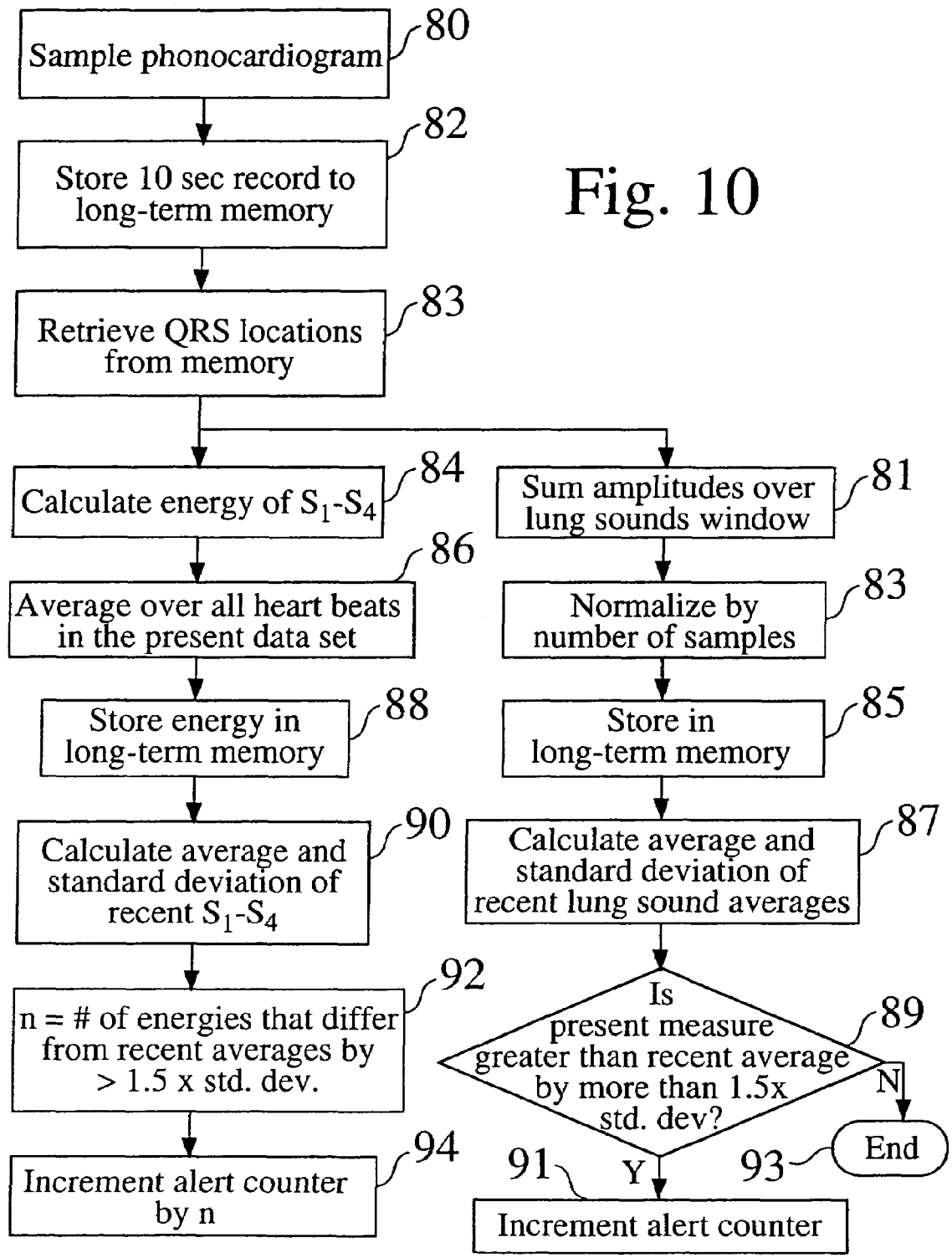
FIG. 10 is a flowchart which describes the processing performed by the electronic circuit on the output of the sound sensor.

In an embodiment the electronic circuit 12 shown in FIG. 1 processes the output of the sound sensor as illustrated in the flow chart of FIG. 10. First, in step 80 the phonocardiogram data is sampled continuously and simultaneously with the ECG signal, preferably at 1 kHz for 5 minutes. Then in step 82 a short segment of the raw data, preferably 10 seconds in length, is stored in long-term storage for later retrieval, thus allowing the physician to review the morphology of the phonocardiogram for signs of an acute heart failure exacerbation. Next, at step 83 the location of each QRS complex is retrieved from memory, having been stored by the electronic circuit when the electronic circuit analyzed the output of the ECG sensor. Next, the energy of the four heart sounds is determined at step 84 by integrating the magnitude of the phonocardiogram signal over windows located relative to the QRS complex. Taking t=0 to be the location of a given QRS complex, in an embodiment S1 is determined by integrating over the window $0<=t<=50$ msec, S2 is determined by integrating over the window $50<=t<=150$ msec, S3 is determined by integrating over the window $150<=t<=250$ msec, S4 is determined by integrating over the window $-200<=t<=0$ msec. These windows may be further optimized using average clinical data or data from a specific patient. In another embodiment the window sizes and locations might be made functions of the RR interval. In still other embodiments, function fitting to the time series, rather than integration, might be performed. For example, the functions $$f_i(t) = \frac{a}{\sqrt{2\pi\sigma^2}} \exp(-(t-b)^2/2\sigma^2)$$

might be fit to the square of the phonocardiogram signal, where $\alpha$ provides a measure of the total energy of the heart sound, b identifies the location of the sound in time, $\sigma$ provides a measure of the sound's duration, and i indicates with which sound $S_i$ the particular function $f_i$ is associated. Still other embodiments might examine heart sound maximum amplitude, average amplitude, integrated amplitude, or duration.

Returning to the embodiment, the heart sound energy measures are respectively averaged at step 86 over all the beats from the present data set, yielding averages for S1–S4. These four values are stored in long-term memory for later retrieval and review by a physician at step 88. The electronic circuit then computes the average and standard deviations of recent heart sound energy values at step 90, preferably using those obtained over the last 24 hours. The number of current heart sound measures that differ from their respective recent average by more than 1.5 times their respective standard deviations is counted at step 92, and this sum is added to the alert counter contained in the electronic circuit at step 94.

Pulmonary rales, which are high-pitched crackles associated with the pulmonary edema of an acute heart failure exacerbation, can be recognized from the sound sensor in a variety of ways. In an embodiment, lung sounds are examined using the portion of the phonocardiogram not covered by the heart sound windows described above, i.e., the interval extending from 250 msec after one QRS complex to 200 msec before the next QRS complex. The average amplitude of the phonocardiogram is calculated by summing the magnitudes of all the samples in all the lung sound windows of the phonocardiogram, step 81 of FIG. 10, and dividing by the total number of samples, step 83. The number of samples is preferably a power of two, so that, as is obvious to one skilled in the art, division is implemented by a right shift. This measure of pulmonary rales is then stored in long-term memory at step 85 for later retrieval and review by a physician. In addition, the electronic circuit computes the average and standard deviations of pulmonary rales measures at step 87, preferably using those obtained over the last 24 hours. If the present pulmonary rales measure differs from the recent average by more than 1.5 times the standard deviations as determined at step 89, then the alert counter contained in the electronic circuit is incremented at step 91, otherwise, computation terminates with step 93.

Other embodiments of the pulmonary rales measure are possible. For example, in one embodiment the analog output of the sound sensor is bandpass filtered, e.g., using a low frequency cutoff of 400 Hz and a high frequency cutoff of 500 Hz, thereby eliminating the heart sounds, which are located below 300 Hz, and providing antialiasing filtering. The signal is then sampled at 1 kHz, and the sum of the magnitudes of each sample is computed. Alternatively, the sum of the squares of each sample can be computed. In another embodiment a higher frequency range is examined, such as 500–3000 Hz. In yet another embodiment the degree of pulmonary rales is quantified by processing in the analog domain. In this embodiment, the output of the sound sensor is rectified and integrated with analog circuits, the design and construction of which are known to those skilled in the art. The integrated output thus serves as the quantitative measure of pulmonary rales.

In alternate embodiments, the presence of pulmonary edema is detected with more direct measures than lung sounds. Thoracic impedance and ultrasound are two specific alternate embodiments. In addition to the changes in respiratory pattern associated with the Cheyne-Stokes respiration of pulmonary edema, described below, which both of these signals can detect, pulmonary edema will cause changes in their baseline readings. Specifically, pulmonary edema will cause a decrease in the baseline thoracic impedance, and an increase in reflected ultrasound signal from the lung fields.

Figure 11:
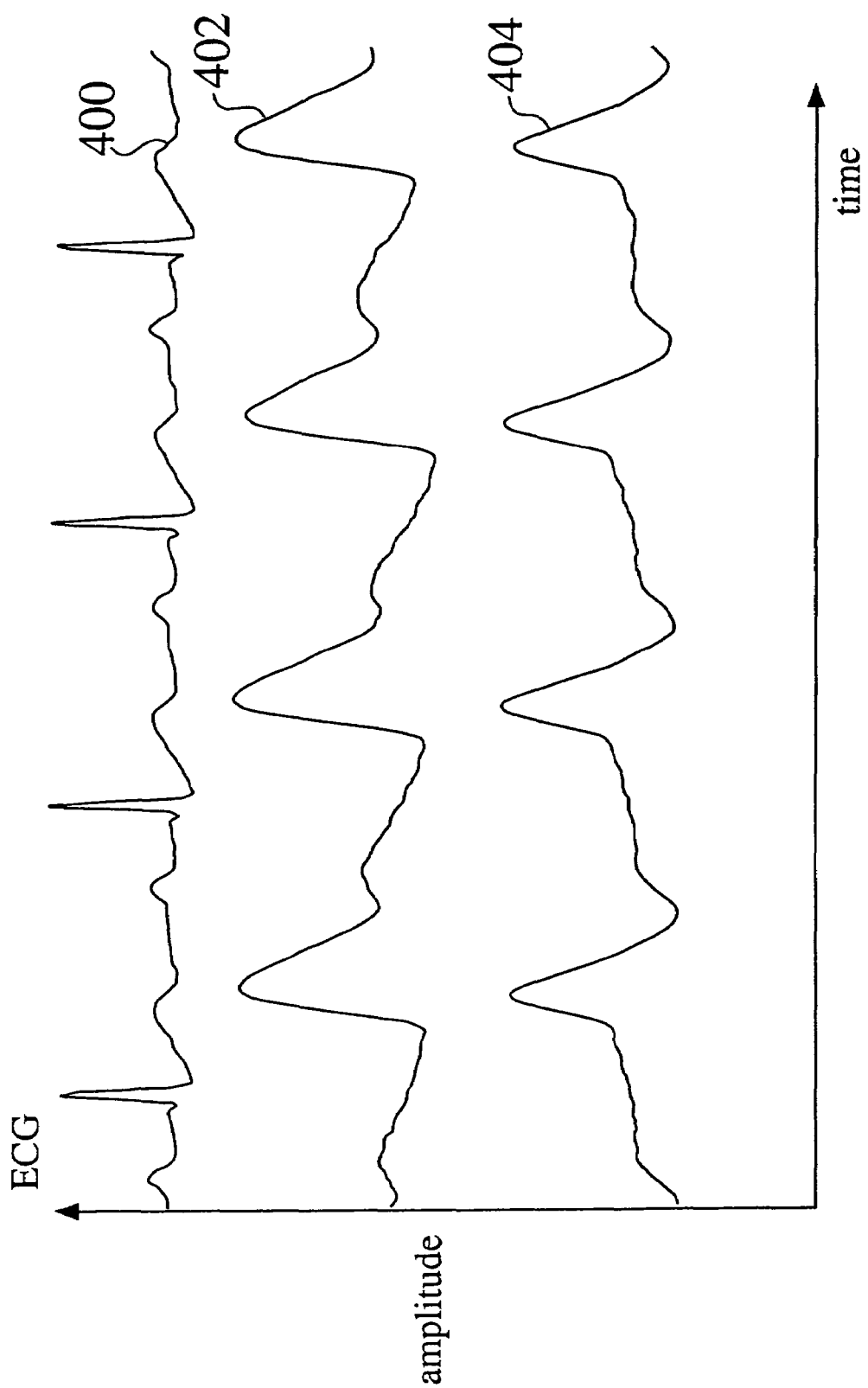
FIG. 11 illustrates the time tracing of the ECG and vascular plethysmograph.

The vascular plethysmograph is preferably obtained using a reflectance optical system, as described above in association with FIG. 5. A typical plethysmograph 402, 404, along with the ECG 400, is illustrated in FIG. 11. The signal 402 obtained using a wide band filter is shown in the middle trace, while the signal 404 obtained using a narrow band filter is shown at the bottom of the figure. To minimize sensitivity to motion, a narrow band filter centered at 15 Hz is preferred.

In a normal resting state, the autonomic nervous system exhibits increased parasympathetic activity and decreased sympathetic activity. The enhanced parasympathetic tone is reflected in greater fluctuations in heart rate. In particular, fluctuations associated with respiration are more pronounced. In contrast, when the body is stressed, as during an acute heart failure exacerbation, sympathetic tone is enhanced, and the respiratory fluctuations are diminished, a property that can be used as a marker of heart failure disease status, as described above in conjunction with FIG. 8. Changes in the autonomic balance can be detected in the pulse signal that is measured using vascular plethysmography. Since the time of the pulse is determined by the time of cardiac contraction, HRV analysis can be applied using the pulse times determined from vascular plethysmography. In this way, an electrical ECG signal is not necessary for HRV analysis. Other alternate embodiments of HRV analysis include those based on heart sounds, ultrasound, mechanical transduction, and pressure transduction, which, like vascular plethysmography and the ECG, can be used to identify the contraction times of the heart.

In addition to the timing of the pulse, the amplitude of the pulse also gives information about the state of the autonomic nervous system. In a normal resting state, when the autonomic nervous system shows increased parasympathetic activity and decreased sympathetic activity, the respiration-associated fluctuations in the output of the autonomic nervous system result in fluctuations in the pulse amplitude that occur in phase with respiration. Slower fluctuations, occurring over 10–30 sec, are also apparent. These likely arise from the well-known Mayer waves, which are naturally occurring 10–30 sec fluctuations in arterial pressure, thought to be due to fluctuations in the degree of vasoconstriction. During stress, as the autonomic nervous system balance favors sympathetic activation, vasoconstriction leads to a reduction in the average pulse amplitude. In addition, both the respiration-associated fluctuations in pulse amplitude and the lower-frequency Mayer waves diminish. Thus, during an acute heart failure exacerbation or general worsening of disease severity, both the pulse amplitude and the variability of the pulse amplitude decrease. These features are used to recognize a developing exacerbation as described below.

Figure 12:
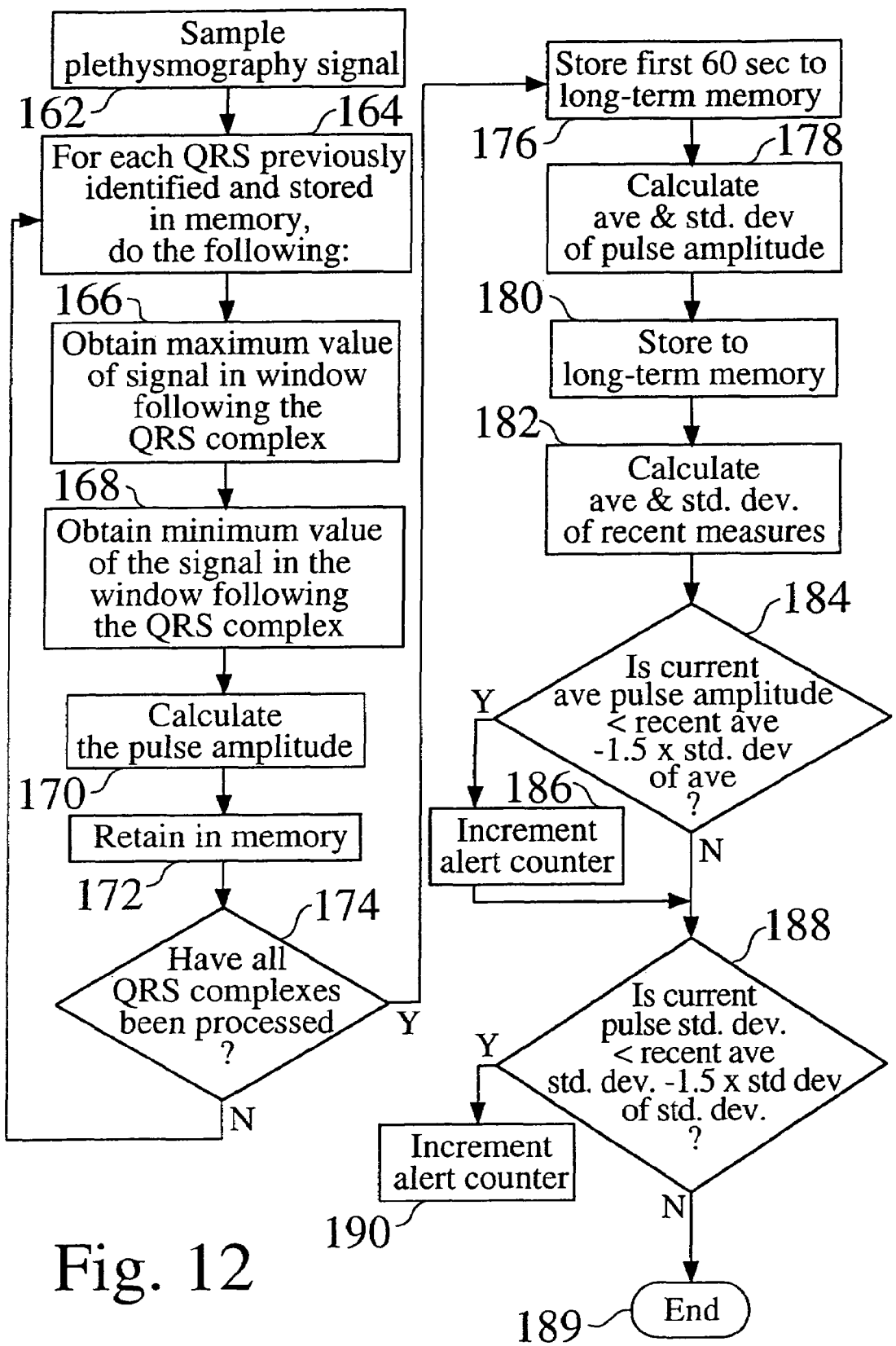
FIG. 12 is a flowchart which describes the processing performed by the electronic circuit on the output of the vascular plethysmography sensor.

The recorded data is processed as illustrated in FIG. 12, in which the increased sympathetic tone associated with an acute heart failure exacerbation or worsening disease status is recognized by detecting a diminution of pulse amplitude and a diminution in pulse amplitude variability. After narrow-band filtering, the plethysmograph is digitally sampled in step 162, preferably synchronously with the ECG previously described. In accordance with an embodiment, 5 minutes of data are acquired. Using the previously stored location of each QRS complex (step 66, FIG. 8) as a marker at step 164, the maximum and minimum values attained by the plethysmography signal in a window following the marker are obtained at steps 166 and 168, respectively. The window length is preferably 200 msec. The difference between the maximum and the minimum is a measure of the pulse amplitude for the given heart beat. It is calculated in step 170, and is retained in memory at step 172. When the end of the data is reached at step 174, a short segment of calculated pulse amplitudes, preferably 60 seconds in length, is stored in long-term storage at step 176 for later retrieval, thus allowing the physician to review the evolution of the pulse amplitude signal. In addition, the average and standard deviation of the pulse amplitude signal is calculated over the entire duration of the recording at step 178. These pulse amplitude measures are then stored in long-term memory for later retrieval and review by a physician at step 180. In addition, the data are analyzed as follows. In general terms, both the pulse amplitude and the variability of the pulse amplitude can be tested for a decrease in magnitude. The pulse amplitude is tested by calculating the average pulse amplitude from the current data set and comparing it to the average pulse amplitude calculated over the last 24 hours.

The comparison is made relative to the standard deviation of the pulse amplitude calculated over the last 24 hours. Similarly, the variability of the pulse amplitude is tested by calculating the standard deviation of the pulse amplitude from the current data set and comparing it to the average standard deviation of the pulse amplitude calculated over the last 24 hours. The comparison is made relative to the standard deviation of the standard deviation of the pulse amplitude calculated over the last 24 hours. Specifically, the electronic circuit computes at step 182 the average and standard deviations of the recent pulse amplitude measures, preferably using those obtained over the last 24 hours. At step 184 the current pulse amplitude average is compared to the average of recently stored values. If it is less than the average by more than 1.5 times the standard deviation of the recent averages, then the alert counter contained in the electronic circuit is incremented at step 186. Similarly, if the current standard deviation is less than the average of recently stored standard deviations by more than 1.5 times the standard deviation of the recent standard deviations, step 188, then the alert counter contained in the electronic circuit is incremented at step 190. Otherwise, the algorithm terminates at step 189.

In accordance with an embodiment, the total variability of pulse amplitude over 5 minutes is calculated. In alternate embodiments, the variability over specific frequency ranges is examined. In particular, the presence of respiratory fluctuations is tested by examining variability in the range 0.17 Hz to 0.4 Hz, and the presence of Mayer waves is tested by examining variability in the range 0.03 Hz to 0.1 Hz. The absence of fluctuations in these frequency bands suggests that disease status is worsening.

Figure 13:
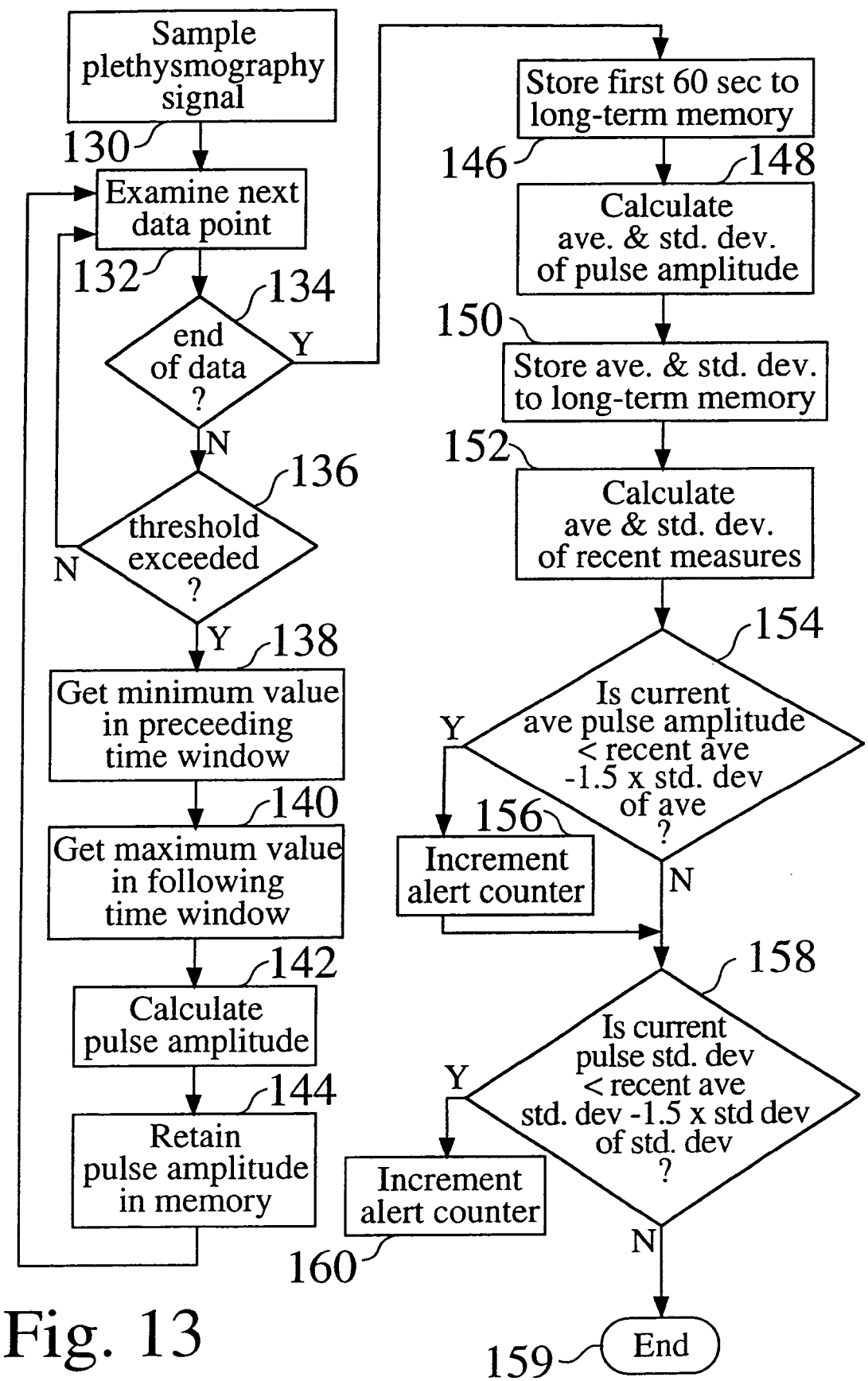
FIG. 13 is a flowchart which describes an alternate embodiment of the processing performed by the electronic circuit on the output of the vascular plethysmography sensor.

An alternate embodiment is possible in which the ECG signal is not used. Rather, as illustrated in FIG. 13, the plethysmography pulses are identified by threshold crossings. After narrow-band filtering, the plethysmograph is digitally sampled in step 130. Proceeding sample by sample through the data at step 132 until the end of the data is reached at step 134, crossings of a predetermined threshold are located at step 136. At each threshold crossing, the minimum value attained by the plethysmography in a preceding time window is located at step 138. Next, at step 140, the maximum valued achieved in a time window following the threshold crossing is located. Both windows are preferably 100 msec. The difference between the maximum and the minimum is a measure of the pulse amplitude for the given heart beat. The difference is calculated in step 142, and is retained in memory at step 144. Once the pulse amplitudes are obtained, i.e., the end of the data is reached at step 134, the remainder of the algorithm follows that of the embodiment described above in association with FIG. 12. Briefly, a short segment of calculated pulse amplitudes is stored in long-term storage at step 146, and the variability of the pulse amplitudes are characterized. Trends in both the amplitude (steps 148, 154) and the variability of the amplitude (steps 148, 158) are determined. Trends toward decreasing pulse amplitude or decreasing amplitude variability are interpreted as reflecting an increase in sympathetic tone, and the alert counter is incremented, steps 156 and 160, respectively.

An alternate embodiment examines the rate of change of vascular volume, rather than the amplitude of the volume change as described above. This signal can be derived in either the analog or digital domain, as is well known to those skilled in the art.

Figure 14:
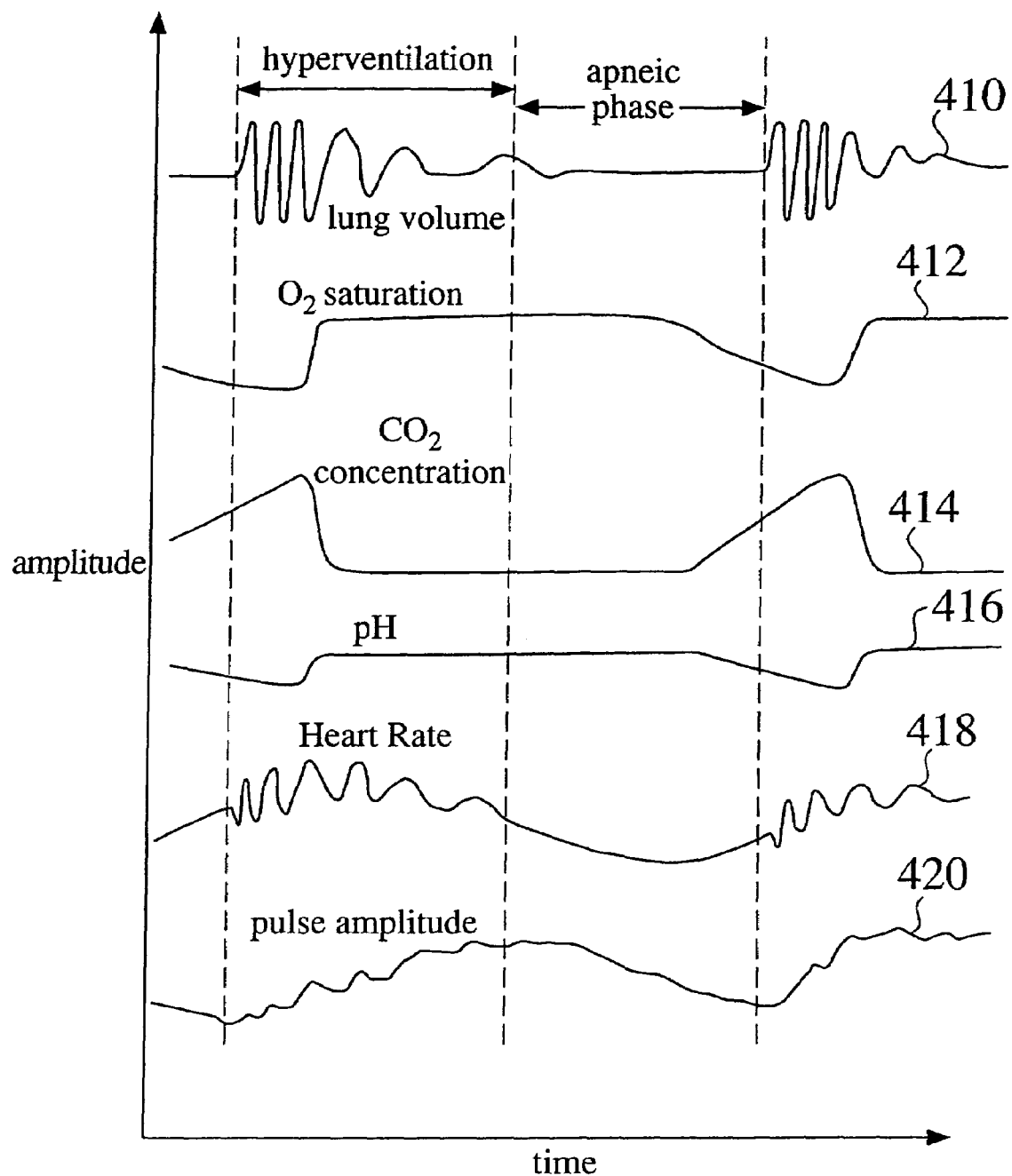
FIG. 14 illustrates the time tracing of the lung volume and various physiologic signals during Cheyne-Stokes respiration.

Another physiologic signal that is useful in assessing hemodynamic status is the respiratory pattern. A characteristic respiratory pattern, called periodic breathing or Cheyne-Stokes respiration, is associated with the declining hemodynamic status of an acute heart failure exacerbation, and is thought to be an indirect result of developing pulmonary edema. As illustrated schematically in FIG. 14 with the tracing of lung volume 410 as a function of time, periods of apnea (absence of breathing) alternate with periods of hyperventilation. During the apneic period, blood $O_2$ saturation 412 falls and blood $CO_2$ content 414 increases. The increasing $CO_2$ levels result in a falling blood pH 416. Since the tissue is in equilibrium with the blood, the changes in chemical concentrations and pH that occur in the blood stream will be detected at the interface between the monitor housing and the tissue. During the apneic phase, as the blood $O_2$ level 412 falls, the autonomic nervous system enters an increasing sympathetic state induced by hypoxia. As illustrated in the figure, the heart rate 418 increases and, due to vasoconstriction induced by the sympathetic state, the pulse amplitude 420 falls, as assessed by vascular plethysmography. Subtle but significant modulation to the average heart rate 418 and pulse amplitude 420 are induced by respiration. During the apneic phase these modulations are absent. Their return marks the onset of the hyperventilation phase. Early in this phase the respiratory oscillations are rapid and of large amplitude. Later in the phase, in concert with the diminishing vigor and rate of respiration, the amplitude and frequency of the heart rate 418 and pulse amplitude 420 oscillations decrease. The Cheyne-Stokes respiratory pattern can thus be detected in a variety of general ways, including methods that directly assess the mechanical changes in the thorax associated with breathing, methods that indirectly assess these changes through their effects on heart rate and pulse amplitude, and methods that measure metabolic gases and chemicals and recognize the oscillatory changes that occur over time scales consistent with the Cheyne-Stokes respiratory pattern.

In accordance with an embodiment, the monitor detects the presence of Cheyne-Stokes respiration using a number of methods. The mechanical changes associated with respiration are assessed using HRV derived from the ECG, the sympathetic/parasympathetic balance is assessed using vascular plethysmography, and the oxygen level of the body is measured using the extravascular blood $O_2$ saturation sensor and the electrochemical tissue $O_2$ sensor. Numerous other methods are possible. The mechanical changes associated with respiration can be detected using impedance plethysmography, a technique well known to those skilled in the art. Ultrasound can be used to determine thoracic diameter and thus estimate lung volume directly. In yet another alternate embodiment respiration is sensed using an pressure transducer placed within the pleural cavity and connected to the implantable hemodynamic monitor. Chemical sensors other than $O_2$ are used in alternate embodiments, such as $CO_2$, pH, and lactic acid.

Figure 15:
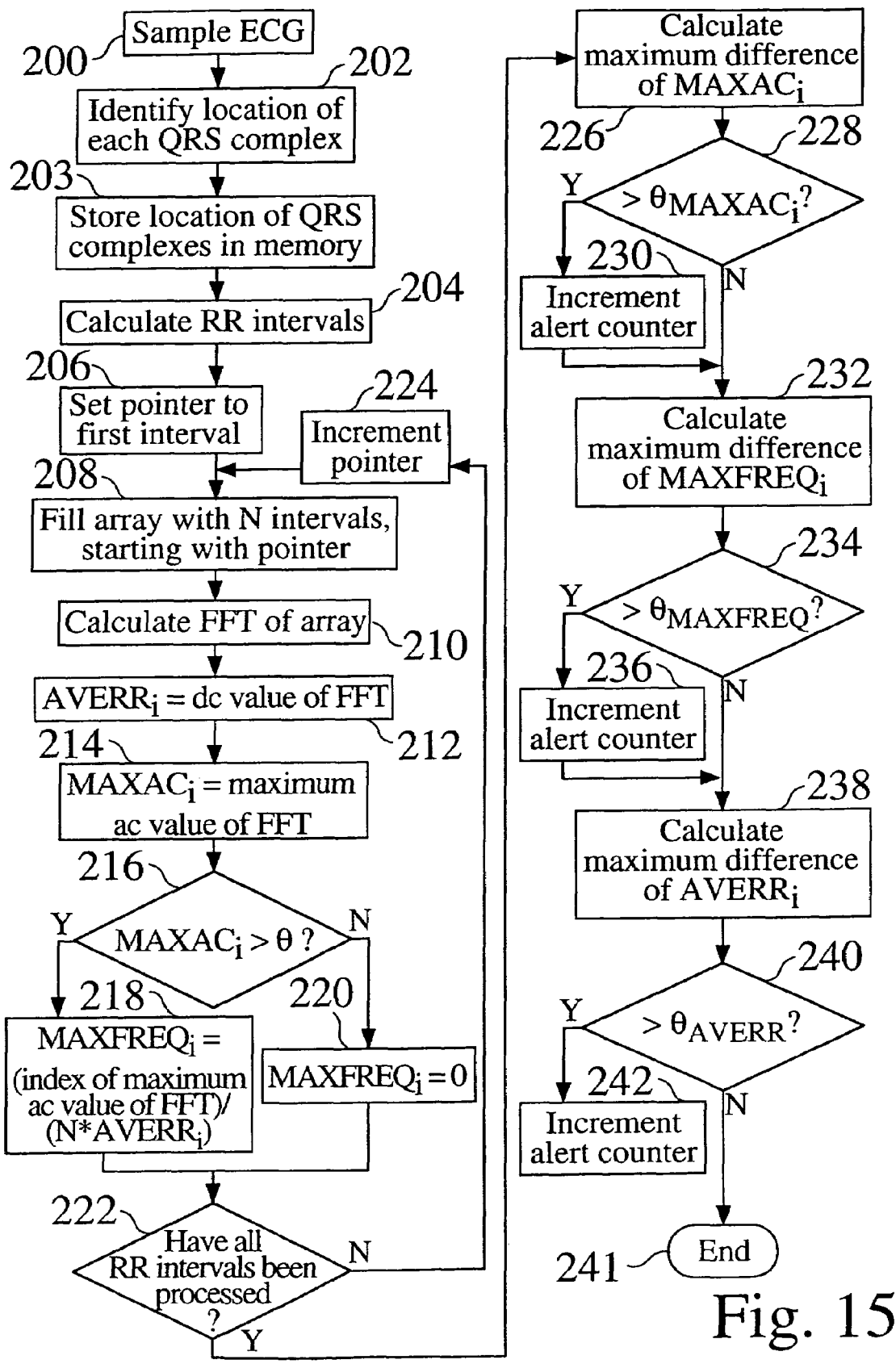
FIG. 15 is a flowchart which describes the processing performed by the electronic circuit on the output of the ECG sensor for the detection of Cheyne-Stokes respiration.

Consider first an embodiment of the assessment of respiratory pattern for the detection of Cheyne-Stokes respiration. As shown in FIG. 15, HRV is used by first sampling the ECG at step 200. The location of each QRS complex is identified in step 202 and is stored in memory at step 203 for later use in the analysis of pulse amplitude, described below. The RR intervals are derived from the QRS complexes in step 204. A pointer is initialized to point to the first RR interval in the sequence at step 206. A temporary array is filled with a predetermined number N of RR intervals in step 208. In an embodiment, N is set equal to 32, which allows subsequent analysis to recognize respiratory rates between 10 and 30 breaths per minute. At step 210, the Fast Fourier Transform (FFT) of the temporary array is obtained, preferably using a special purpose digital signal processing integrated circuit. At step 212, the average RR interval over the data in the temporary array is taken from the dc value of the FFT result and assigned to the variable $AVERR_i$. The maximum ac component of the FFT result is assigned to the variable $MAXAC_i$ at step 214. If this value is greater than a predetermined threshold θ then the variable $MAXFREQ_i$ is assigned the corresponding frequency as shown in step 218, otherwise, it is assigned the value zero, as shown in step 220. The test of whether all RR intervals have been processed is performed at step 222. If not, then the pointer is incremented at step 224, and control returns to step 208. If all RR intervals have been processed, then control continues at step 226, where all values of $MAXAC_i$ are examined to calculate the maximum difference in respiratory amplitude during the present analysis. If this difference is greater than a predetermined threshold $\theta_{MAXAC}$, tested at step 228, then the alert counter is incremented at step 230. Next, at step 232, the maximum difference in the respiratory frequency is calculated. If this difference is greater than a predetermined threshold $\theta_{MAXFREQ}$, tested at step 234, then the alert counter is incremented at step 236. Finally, at step 238, the maximum difference in the average RR interval is calculated. If this difference is greater than a predetermined threshold $\theta_{AVERR}$, tested at step 240, then the alert counter is incremented at step 242, otherwise, the algorithm terminates at step 241. As will be obvious to one skilled in the art, there are a variety of alternate possible embodiments of the analysis of HRV for the assessment of respiratory pattern.

Figure 16:
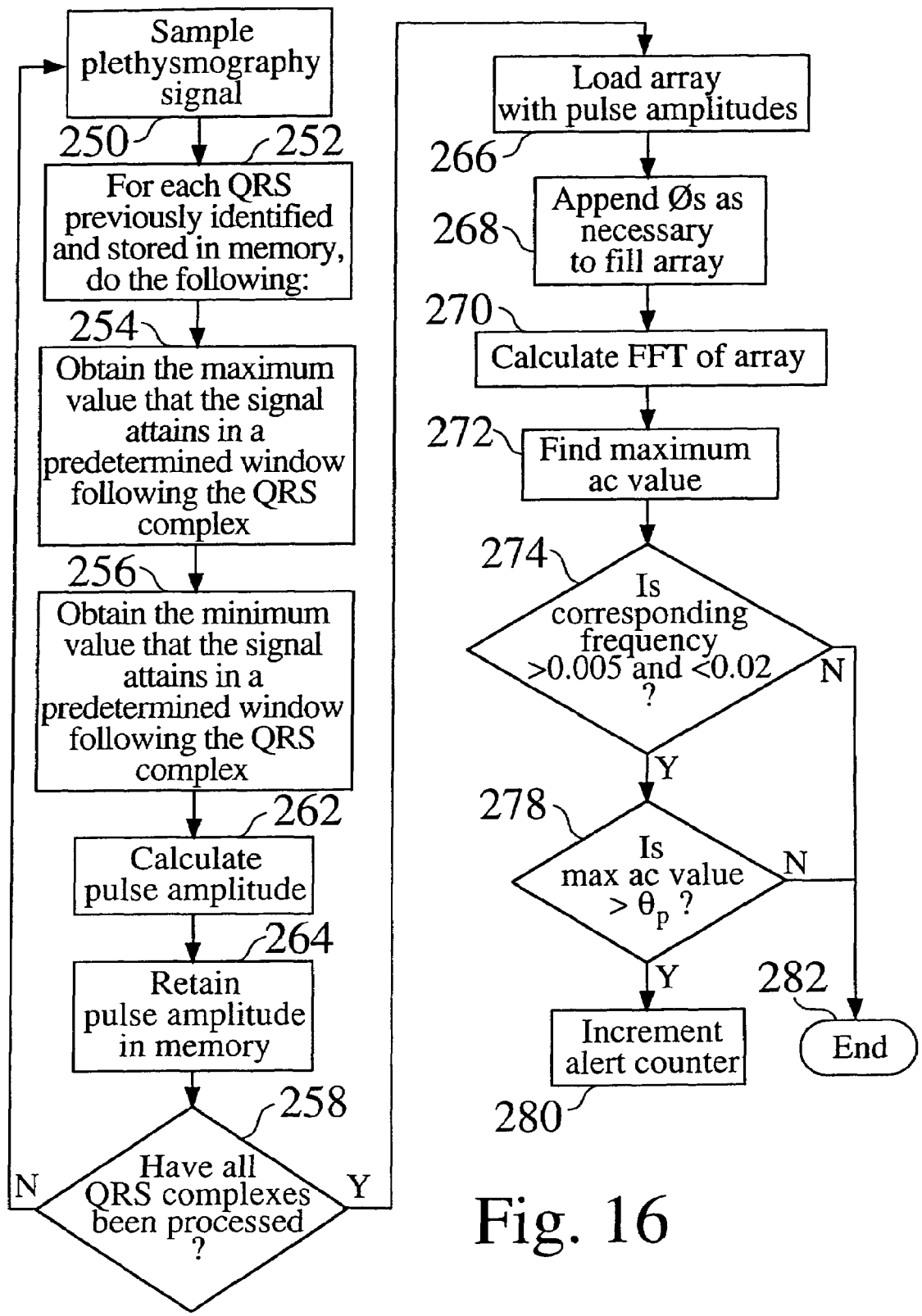
FIG. 16 is a flowchart which describes the processing performed by the electronic circuit on the output of the vascular plethysmography sensor for the detection of Cheyne-Stokes respiration.

Considering next the analysis of the sympathetic/parasympathetic balance assessed by vascular plethysmography, we note that in the context of Cheyne-Stokes respiration, oscillations in the sympathetic/parasympathetic balance that occur on the order of a few minutes are of interest. This is in contrast to longer-term and slower shifts in the sympathetic/parasympathetic balance, the analysis of which was described above in reference to FIGS. 8, 12, and 13. The analysis is presented in FIG. 16, where after narrow-band filtering, the plethysmograph is digitally sampled in step 250, preferably of 10 minutes duration and synchronously with the ECG previously described. Using the previously stored location of each QRS complex (step 203, FIG. 15) as a marker, the maximum and minimum values attained by the plethysmography signal in a window following the marker are obtained at steps 254 and 256, respectively. The window length is preferably 200 msec. The difference between the maximum and the minimum is a measure of the pulse amplitude for the given heart beat. It is calculated in step 262, and is retained in memory at step 264. When the end of the data is reached at step 258, the calculated pulse amplitudes are fetched from memory and loaded into an array, shown in step 266. Since the FFT algorithm requires $2^n$ data points, zeros are appended as necessary as shown in step 268, a process known as zero padding and well-known to those familiar with the art. Next, at step 270, the FFT is computed, preferably using a special-purpose digital signal processing integrated circuit. The results are analyzed in step 272 in order to identify the frequency component with the greatest amplitude. If, as tested in step 274, the frequency corresponding to this component lies between 0.005 and 0.02 Hz, the frequency range associated with Cheyne-Stokes respiration, and if, as tested in step 278, the amplitude of this maximum component exceeds a predetermined threshold, then the alert counter is incremented at step 280. As will be obvious to one skilled in the art, a variety of alternate embodiments of the analysis of respiratory pattern exist.

Figure 17:
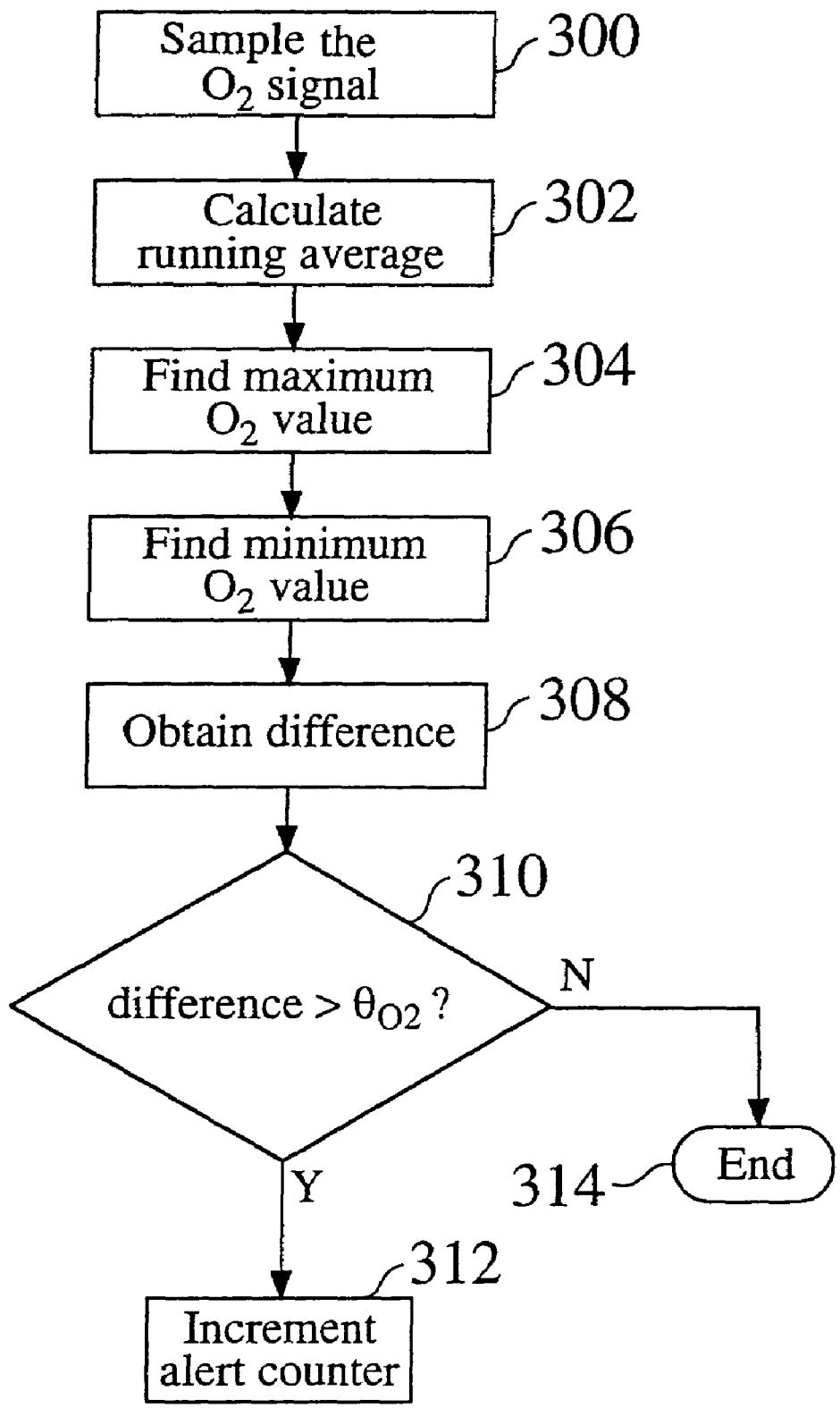
FIG. 17 is a flowchart which describes the processing performed by the electronic circuit on the output of the oxygen saturation and oxygen partial pressure sensors for the detection of Cheyne-Stokes respiration.

Finally, turning to the detection of Cheyne-Stokes respiration using the blood $O_2$ saturation sensor and the tissue electrochemical $O_2$ sensor, in an embodiment both of these signals are analyzed according to the same algorithm. Consequently, the algorithm is described with reference to a generic $O_2$ sensor. As shown in FIG. 17, the $O_2$ signal is first digitally sampled in step 300 using the preferred sampling rate of 500 Hz. A running average is computed in step 302, thereby minimizing high frequency artifacts. The preferred window length for the running average is approximately 1 sec. Next, the maximum and minimum values attained by the $O_2$ signal are determined, as shown in steps 304 and 306, respectively. The difference between these is calculated, step 308, and if greater than the predetermined threshold $\theta_{O2}$, tested at step 310, the alert counter is incremented, step 312, otherwise, the algorithm terminates, step 314.

In an alternate embodiment, the number of periods of apnea occurring in a predetermined interval, such as 30 minutes, is counted. An increasing number of apneic periods indicates that disease status is worsening.

In still another alternate embodiment, the severity of the apnea is assessed by the duration of the apneic episode.

Still another embodiment recognizes the oscillations in respiratory depth and rate that occur with periodic breathing in the absence of true apnea. The frequency of the oscillations, the magnitude of change between deep and shallow breathing, and the change in respiratory rate are used as markers for disease severity.

Figure 18:
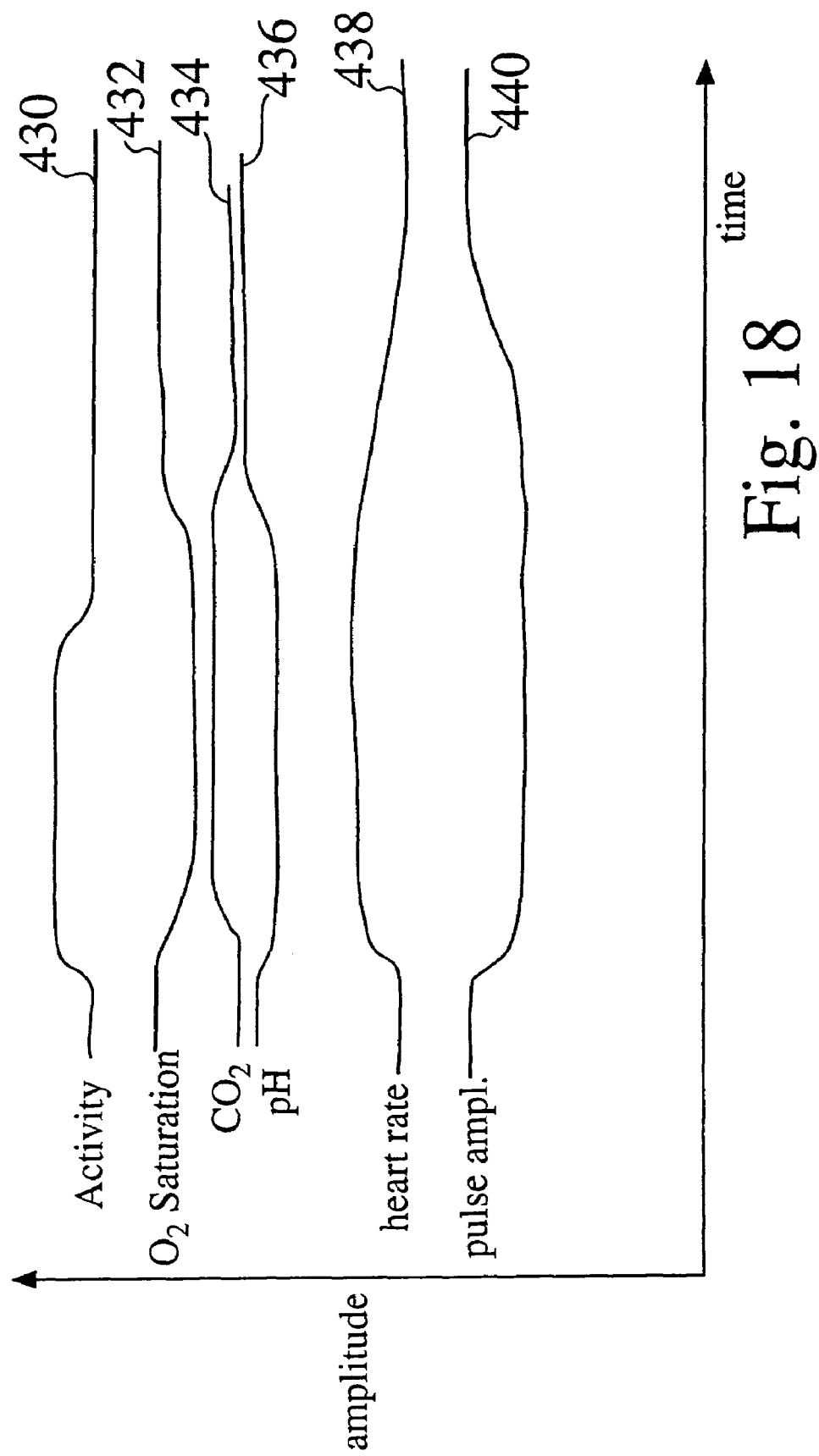
FIG. 18 illustrates the time tracing of various physiologic signals during activity-induced desaturation of hemoglobin.

In Cheyne-Stokes respiration, the saturation of hemoglobin with oxygen decreases because respiration ceases during the apneic phase. A different mechanism can also lead to the partial desaturation of hemoglobin. In this second mechanism desaturation is associated with activity. For a patient in acute heart failure, hemodynamic status is in a tenuous balance. The relatively minor increased demand of simple physical activity, such as walking across a room, can be enough to exceed the hemodynamic reserve. This process is exacerbated by the presence of pulmonary edema, which hinders the oxygenation of blood in the lungs. Thus, as illustrated in FIG. 18, an increase in physical activity 430 is associated with a decrease in $O_2$ saturation 432. As the $O_2$ level of the blood falls, the body resorts to anaerobic metabolism, which increases the level of lactic acid in the blood. The resulting acidemia is reflected in the falling pH 436, a process which is partially attenuated by the buffering action of the blood, in which free hydrogen combines with bicarbonate ion to yield $CO_2$ and water, thus increasing the $CO_2$ concentration 434 in the blood. At the same time, because of the increased sympathetic drive induced by hypoxia, the heart rate 438 increases and the pulse amplitude 440 decreases.

Figure 19:
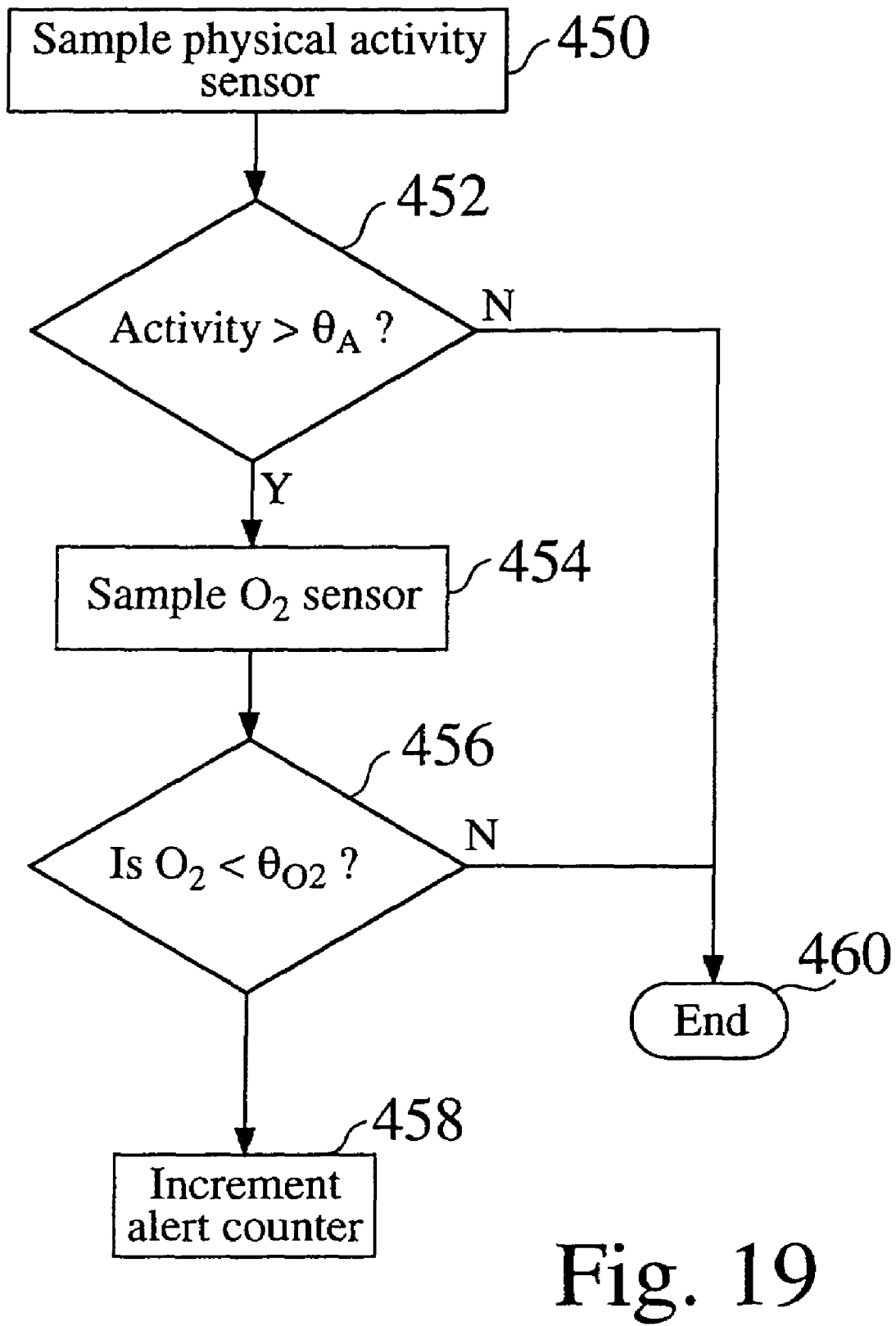
FIG. 19 is a flowchart which describes the algorithm used for detecting activity-related decrease in oxygen.

As suggested by FIG. 18, physical-activity-associated desaturation can be detected by monitoring a variety of physiological signals, including $CO_2$ concentration, pH, heart rate, and pulse amplitude. In accordance with an embodiment, activity-related desaturation is detected by simultaneously monitoring the outputs of an activity sensor and an arterial hemoglobin saturation sensor. In contrast to the embodiments relating to the analysis of the other sensors, which were conditioned on the patient being at rest, as described above, the present analysis is conditioned on the patient being active. As illustrated in FIG. 19, the output of a physical activity sensor is sampled at step 450 and compared to a predetermined threshold $\theta_A$ at step 452. If the threshold is not exceeded, the algorithm terminates 460. Otherwise, the output of the $O_2$ sensor is sampled 454 and compared to a predetermined threshold $\theta_{O2}$ at step 456. If $O_2$ level is below the threshold then the alert counter is incremented in step 458, otherwise, the algorithm is terminated at 460.

Figure 20:
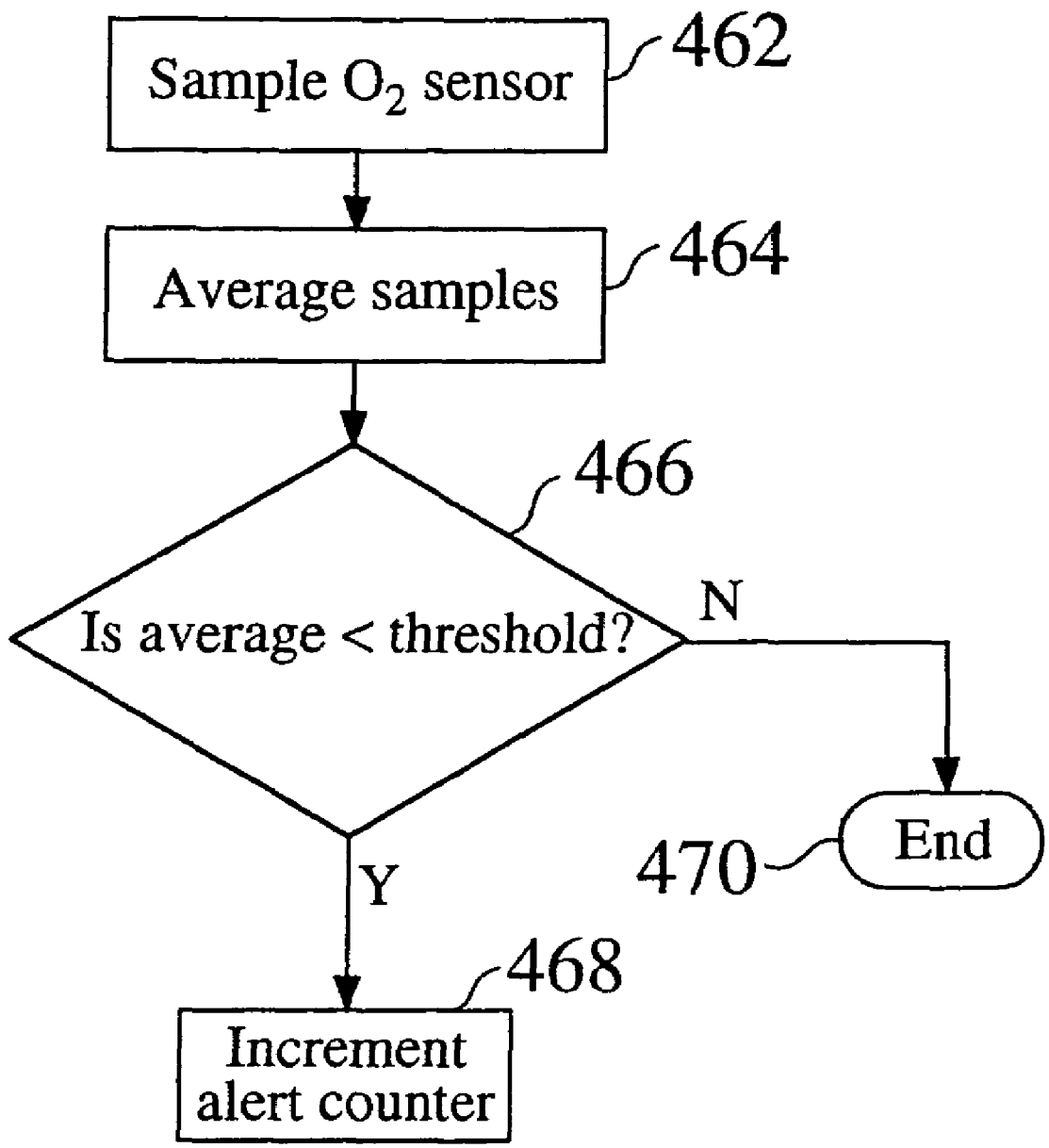
FIG. 20 is a flowchart which describes the algorithm used for the unconditioned detection of a decrease in oxygen.

Desaturation of hemoglobin is a nonspecific event. As described above in association with FIG. 14 it can be due to lack of respiration in the apneic phase of Cheyne-Stokes respiration, or as just described in association with FIG. 18 it can be due to increased physical activity and insufficient hemodynamic reserve. There are other causes for intermittent desaturation in addition to these. For example, the formation of a mucus plug in a pulmonary bronchiole or bronchus can lead to partial desaturation, a process which does not necessarily reflect the underlying hemodynamic status. In an embodiment, the detection of Cheyne-Stokes-associated desaturation is conditioned on the patient being at rest, and the detection of activity-associated desaturation is conditioned on the patient being active. Conditioning the analysis in this way improves the specificity of the detection algorithm. In an embodiment, one additional analysis of the $O_2$ sensor is performed in which the analysis is not conditioned on other factors such as activity. Increments to the alert counter from this algorithm are thus less specific than from other sources, but because conditioning is not imposed they are more sensitive. In an embodiment the oxygen sensor used by this algorithm is the arterial hemoglobin saturation sensor. Other sensors such as the electrochemical $O_2$ sensor can be used, but the arterial hemoglobin saturation sensor is advantageous because it provides data that are more readily interpreted by a clinician. The algorithm is presented in FIG. 20, where the output of the $O_2$ sensor is first sampled at step 462 then averaged, step 464. If the average is below a predetermined threshold at step 466 then the alert counter is incremented at step 468, otherwise, the algorithm is terminated at step 470.

Devices that include a light source 26 and a light detector 28, which are useful for producing a plethysmography signal (and more specifically, a photo-plethysmography signal) were described in detail above, e.g., with reference to FIGS. 2C, 3C and 5a–5d. Also described above was how such a photo-plethysmography signal could be used to monitor the autonomic tone of a patient. Measures of autonomic tone could be used, for example, to provide an indication of the progression of the disease state of the patient, as has been explained. The high level flowchart of FIG. 21 will now be used to summarize how a photo-plethysmography signal can be used to monitor autonomic tone.

Figure 21:
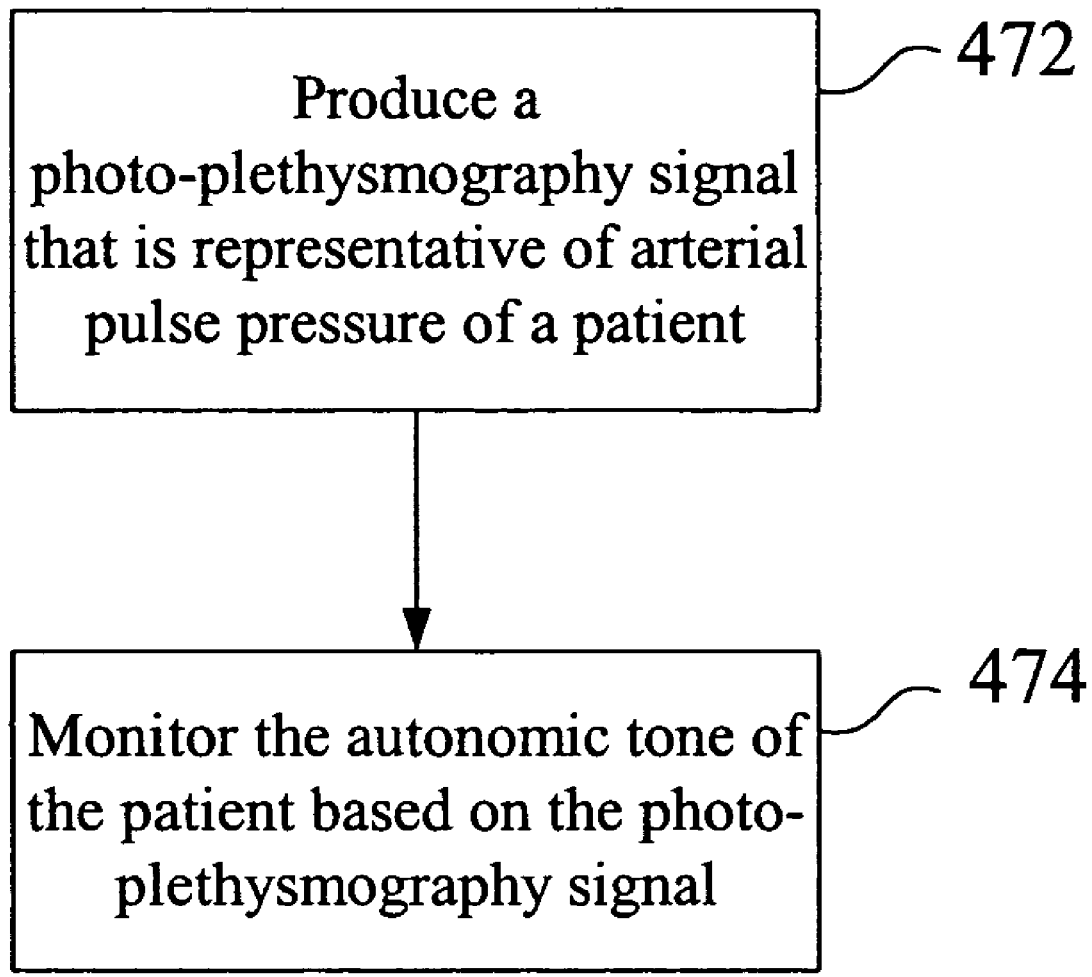
FIG. 21 is a flowchart that is useful for summarizing embodiments of the present invention in which a photo-plethysmography signal is used to monitor autonomic tone of a patient.

Referring to FIG. 21, at step 472, a photo-plethysmography signal is produced. Photo-plethysmography directly detects changes in arterial and venous volume, and consequently can indirectly detect changes in mean arterial pressure and arterial pulse pressure. The photo-plethysmography signal can be produced using a light source and a light detector, that are extravascularly implanted in the patient, as was explained above. Alternatively, a light source and a light detector, that are not implanted in a patient, can be used to produce the photo-plethysmography signal, as was also explained above.

At step 474, the autonomic tone of the patient is monitored based on the photo-plethysmography signal. This can include, identifying changes in at least one of sympathetic tone and parasympathetic tone of the patient, based on changes in pulse amplitude associated with the photo-plethysmography signal.

In accordance with embodiments of the present invention, measures of pulse amplitude are obtained from the photo-plethysmography signal, and changes in the sympathetic tone of the patient are recognized based changes in the measures of pulse amplitude. For example, this can include: recognizing an increase in pulse amplitude as a decrease in the sympathetic tone of the patient; recognizing an increase in pulse amplitude variability as a decrease in the sympathetic tone of the patient; recognizing a decrease in pulse amplitude as an increase in the sympathetic tone of the patient; and/or recognizing a decrease in pulse amplitude variability as an increase in the sympathetic tone of the patient.

In accordance with embodiments of the present invention, changes in parasympathetic tone of the patient are recognized based changes in the measures of pulse amplitude. For example, this can include: recognizing an increase in pulse amplitude as an increase in the parasympathetic tone of the patient; recognizing an increase in pulse amplitude variability as an increase in the parasympathetic tone of the patient; recognizing a decrease in pulse amplitude as a decrease in the parasympathetic tone of the patient; and/or recognizing a decrease in pulse amplitude variability as a decrease in the parasympathetic tone of the patient.

In accordance with further embodiments of the present invention, the measures of autonomic tone, produced based on a photo-plethysmography signal, are used for pacing interval optimization. This can be accomplished by using the measures of autonomic, which are based on a photo-plethysmography signal, as measures of cardiac performance. Such embodiments are summarized below, with reference to FIG. 24. However, FIGS. 22 and 23 are first used to describe an exemplary stimulation device that can be used for pacing and pacing interval optimization.

Figure 22:
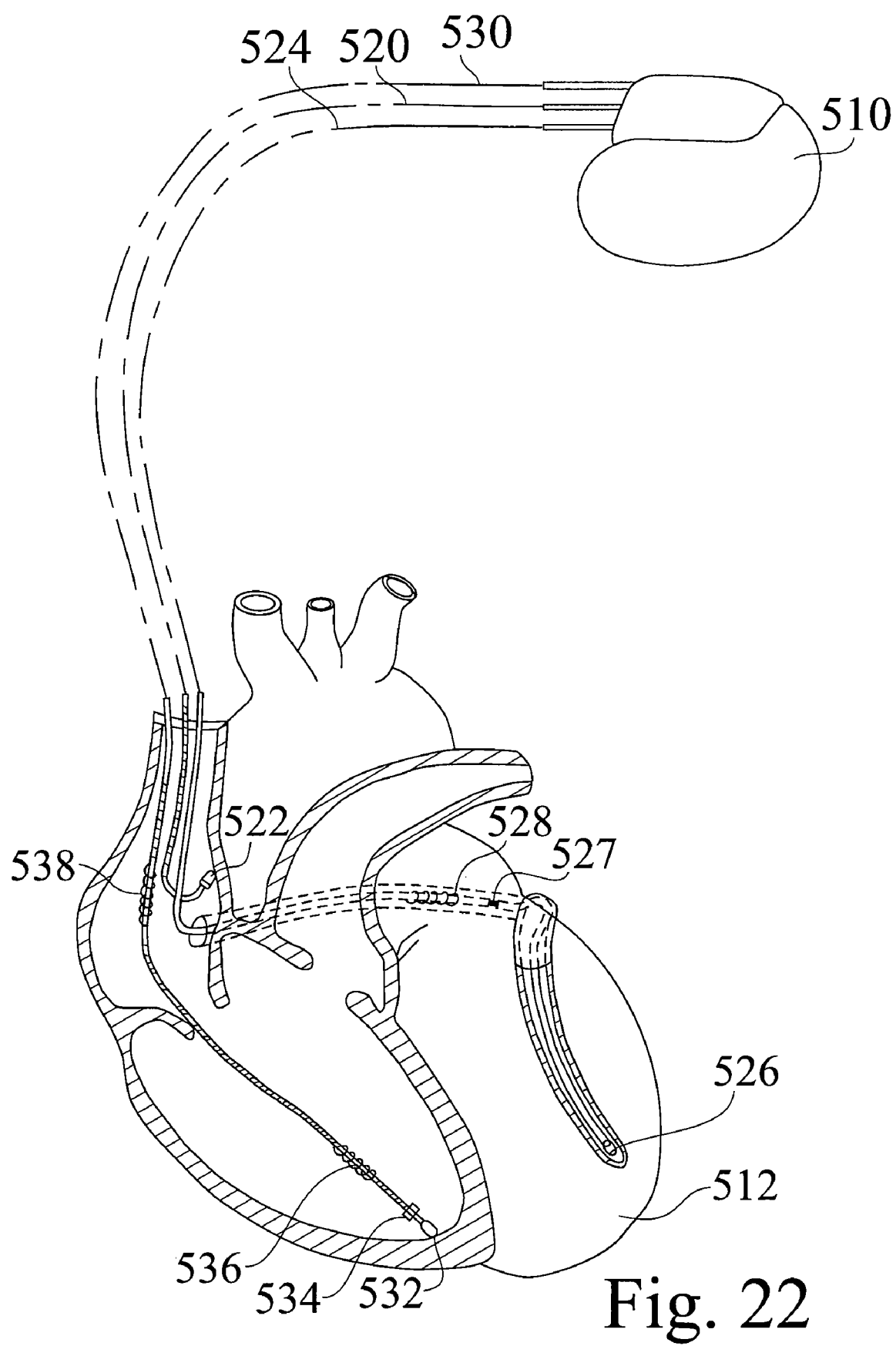
FIG. 22 is a simplified diagram illustrating an implantable stimulation device in electrical communication with at least three leads implanted into a patient's heart for delivering multi-chamber stimulation and shock therapy.
Figure 23:
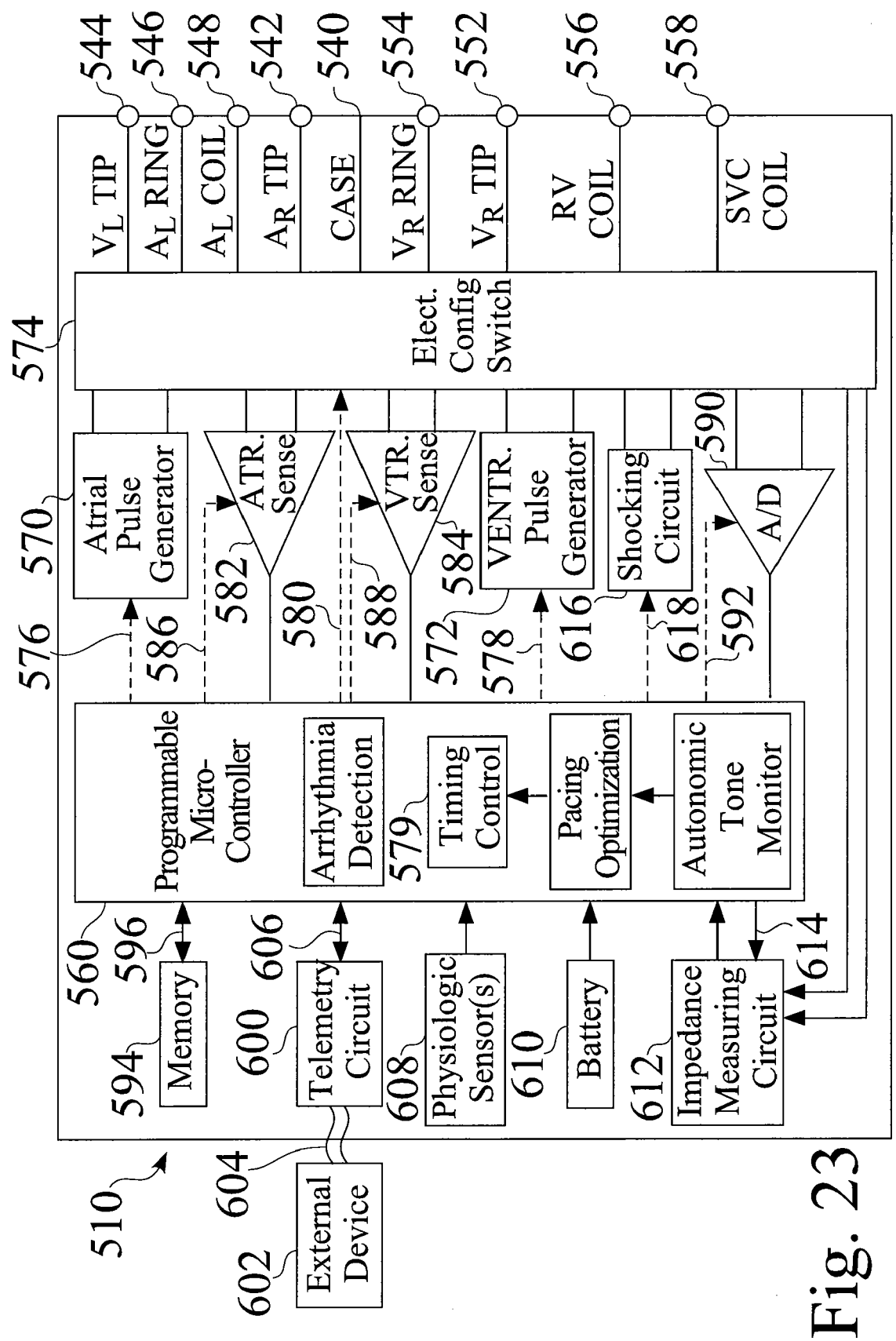
FIG. 23 is a functional block diagram of a multi-chamber implantable stimulation device illustrating the basic elements of a stimulation device which can provide cardioversion, defibrillation and pacing stimulation in four chambers of the heart.

Referring to FIG. 22, an exemplary implantable stimulation device 510 (also referred to as a pacing device, or a pacing apparatus) is in electrical communication with a patient's heart 512 by way of three leads, 520, 524 and 530, suitable for delivering multi-chamber stimulation and shock therapy. To sense atrial cardiac signals and to provide right atrial chamber stimulation therapy, the stimulation device 510 is coupled to an implantable right atrial lead 520 having at least an atrial tip electrode 522, which typically is implanted in the patient's right atrial appendage. Stimulation device 510 can be integrated with one of the embodiments of the monitor 20 discussed above. That is, a common housing can be used to containing the elements of the monitor 20 (e.g., a light source 26 and light detector 28) and the elements of the stimulation device 510. Alternatively, separates housings can be used to house the monitor 20 and the stimulation device 510. This is of course necessary if a monitor in not implantable (e.g., in embodiments where the one or more sensors associated with a monitor are incorporated into a finger cuff, a wristband, a configuration resembling a watch, or a configuration resembling a clip-on earring).

Referring to FIG. 22, to sense left atrial and ventricular cardiac signals and to provide left-chamber pacing therapy, the stimulation device 510 is coupled to a "coronary sinus" lead 524 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 524 is designed to receive atrial and ventricular cardiac signals and to deliver left ventricular pacing therapy using at least a left ventricular tip electrode 526, left atrial pacing therapy using at least a left atrial ring electrode 527, and shocking therapy using at least a left atrial coil electrode 528.

The stimulation device 510 is also shown in electrical communication with the patient's heart 512 by way of an implantable right ventricular lead 530 having, in this embodiment, a right ventricular tip electrode 532, a right ventricular ring electrode 534, a right ventricular (RV) coil electrode 536, and an SVC coil electrode 538. Typically, the right ventricular lead 530 is transvenously inserted into the heart 512 so as to place the right ventricular tip electrode 532 in the right ventricular apex so that the RV coil electrode 536 will be positioned in the right ventricle and the SVC coil electrode 538 will be positioned in the superior vena cava. Accordingly, the right ventricular lead 530 is capable of receiving cardiac signals and delivering stimulation in the form of pacing and shock therapy to the right ventricle.

As illustrated in FIG. 23, a simplified block diagram is shown of the multi-chamber implantable stimulation device 510, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 540 for the stimulation device 510, shown schematically in FIG. 23, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 544, 546, 548, 552, 554, 556, and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522.

To achieve left chamber sensing, pacing and shocking, the connector includes at least a left ventricular tip terminal ($V_L$ TIP) 544, a left atrial ring terminal ($A_L$ RING) 546, and a left atrial shocking terminal ($A_L$ COIL) 48, which are adapted for connection to the left ventricular ring electrode 526, the left atrial tip electrode 527, and the left atrial coil electrode 528, respectively.

To support right chamber sensing, pacing and shocking, the connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558, which are adapted for connection to the right ventricular tip electrode 532, right ventricular ring electrode 534, the RV coil electrode 536, and the SVC coil electrode 538, respectively. At the core of the stimulation device 510 is a programmable microcontroller 560 which controls the various modes of stimulation therapy. As is well known in the art, the microcontroller 560 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design of the microcontroller 560 are not critical to the present invention. Rather, any suitable microcontroller 560 can be used to carry out the functions described herein. The use of microprocessor-based control circuits for performing timing and data analysis functions are well known in the art. In specific embodiment of the present invention, the microcontroller 560 performs some or all of the steps associated with determining optimal pacing parameters in accordance with the present invention. The microcontroller 560 can also be used to monitor autonomic tone, in those embodiments where components of the monitor 20 (such as a light source and light detector) are integrated with the stimulation device 510.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 23, an atrial pulse generator 570 and a ventricular pulse generator 572 generate pacing stimulation pulses for delivery by the right atrial lead 520, the right ventricular lead 530, and/or the coronary sinus lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators, or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry 579 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay The switch bank 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, coronary sinus lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers, or shared amplifiers. The switch 574 determines the "sensing polarity" of the cardiac signal by selectively closing the appropriate switches, as is also known in the art. In this way, the clinician may program the sensing polarity independent of the stimulation polarity.

Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables the device 510 to deal effectively with the difficult problem of sensing the low amplitude signal characteristics of atrial or ventricular fibrillation. Such sensing circuits, 582 and 584, can be used to determine cardiac performance values used in the present invention.

The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity, in the appropriate chambers of the heart. The sensing circuits, 582 and 584, in turn, receive control signals over signal lines, 586 and 588, from the microcontroller 560 for purposes of measuring cardiac performance at appropriate times, and for controlling the gain, threshold, polarization charge removal circuitry (not shown), and timing of any blocking circuitry (not shown) coupled to the inputs of the sensing circuits, 582 and 586.

For arrhythmia detection, the device 510 utilizes the atrial and ventricular sensing circuits, 582 and 584, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the coronary sinus lead 524, and the right ventricular lead 530 through the switch 574 to sample cardiac signals across any pair of desired electrodes.

Advantageously, the data acquisition system 590 can be coupled to the microcontroller, or other detection circuitry, for detecting an evoked response from the heart 512 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 560 detects a depolarization signal during a window following a stimulation pulse, the presence of which indicates that capture has occurred. The microcontroller 560 enables capture detection by triggering the ventricular pulse generator 572 to generate a stimulation pulse, starting a capture detection window using the timing control circuitry 579 within the microcontroller 560, and enabling the data acquisition system 590 via control signal 592 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 560 is further coupled to a memory 594 by a suitable data/address bus 596, wherein the programmable operating parameters used by the microcontroller 560 are stored and modified, as required, in order to customize the operation of the stimulation device 510 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 512 within each respective tier of therapy.

A feature of the present invention is the ability to sense and store a relatively large amount of data (e.g., from the data acquisition system 590). Such data can then be used for subsequent analysis to guide the programming of the device and/or to appropriately adjust pacing parameters in accordance with embodiments of the present invention.

Advantageously, the operating parameters of the implantable device 510 may be non-invasively programmed into the memory 594 through a telemetry circuit 600 in telemetric communication with the external device 602, such as a programmer, transtelephonic transceiver, or a diagnostic system analyzer. The telemetry circuit 600 is activated by the microcontroller by a control signal 606. The telemetry circuit 600 advantageously allows intracardiac electrograms and status information relating to the operation of the device 510 (as contained in the microcontroller 560 or memory 594) to be sent to an external device 602 through an established communication link 604.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In accordance with an embodiment, the stimulation device 510 further includes one or more physiologic sensors 608, that can be used to detect changes in cardiac performance or changes in the physiological condition of the heart. The physiologic sensors 608 can include, for example, a light source and a light detector (e.g., similar to light source 26 and light detector 28). In other words, portions of the monitor 20, described in detail above, can be incorporated into or with the stimulation device 510. This would enable the stimulation device 510 to produce a photo-plethysmography signal that is useful for measuring pulse amplitudes and monitoring autonomic tone of a patient. The microcontroller 560 can respond by selecting and/or adjusting the various pacing parameters (e.g., atrio-ventricular delay, interventricular delay, interatrial delay etc.), based on measures of the photo-plethysmography signal. For example, as will be described in more detail below, the microcontroller 560 may adjust pacing parameters based on measures of autonomic tone, or more specifically based on measures of pulse amplitude. Other examples of physiological sensors 608 that are useful for detecting changes in cardiac performance include a pressure transducer, an accelerometer or a microphone that can detect heart sounds, or an ultrasound transducer.

The microcontroller 560 can respond to measures of cardiac performance by adjusting the various pacing parameters in accordance with the embodiments of the present invention. The microcontroller 560 controls adjustments of pacing parameters by, for example, controlling the stimulation pulses generated by the atrial and ventricular pulse generators, 570 and 572. While shown as being included within the stimulation device 510, it is to be understood that the physiologic sensor 608 may also be external to the stimulation device 510, yet still be implanted within or carried by the patient. More specifically, the sensor 608 can be located inside the device 510, on the surface of the device 510, in a header of the device 510, or on a lead (which can be placed inside or outside the bloodstream).

The stimulation device 510 additionally includes a battery 610 which provides operating power to all of the circuits shown in FIG. 23. For the stimulation device 510, which employs shocking therapy, the battery 610 must be capable of operating at low current drains for long periods of time, and then be capable of providing high-current pulses (for capacitor charging) when the patient requires a shock pulse. The battery 510 must also have a predictable discharge characteristic so that elective replacement time can be detected. Accordingly, the device 510 preferably employs lithium/silver vanadium oxide batteries, as is true for most (if not all) current devices.

The stimulation device 510 further includes a magnet detection circuitry (not shown), coupled to the microcontroller 560. It is the purpose of the magnet detection circuitry to detect when a magnet is placed over the stimulation device 510, which magnet may be used by a clinician to perform various test functions of the stimulation device 10 and/or to signal the microcontroller 560 that the external programmer 602 is in place to receive or transmit data to the microcontroller 560 through the telemetry circuits 100.

As further shown in FIG. 23, the device 510 is shown as having an impedance measuring circuit 612 which is enabled by the microcontroller 560 via a control signal 614. The known uses for an impedance measuring circuit 620 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 620 is advantageously coupled to the switch 574 so that any desired electrode may be used. The impedance measuring circuit 612 is not critical to the present invention and is shown only for completeness.

In the case where the stimulation device 510 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 Joules), moderate (0.5–10 Joules), or high energy (11 to 40 Joules), as controlled by the microcontroller 560. Such shocking pulses are applied to the patient's heart 512 through at least two shocking electrodes, and as shown in this embodiment, selected from the left atrial coil electrode 528, the RV coil electrode 536, and/or the SVC coil electrode 538. As noted above, the housing 540 may act as an active electrode in combination with the RV electrode 536, or as part of a split electrical vector using the SVC coil electrode 538 or the left atrial coil electrode 528 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, the microcontroller 560 is capable of controlling the synchronous or asynchronous delivery of the shocking pulses.

Figure 24:
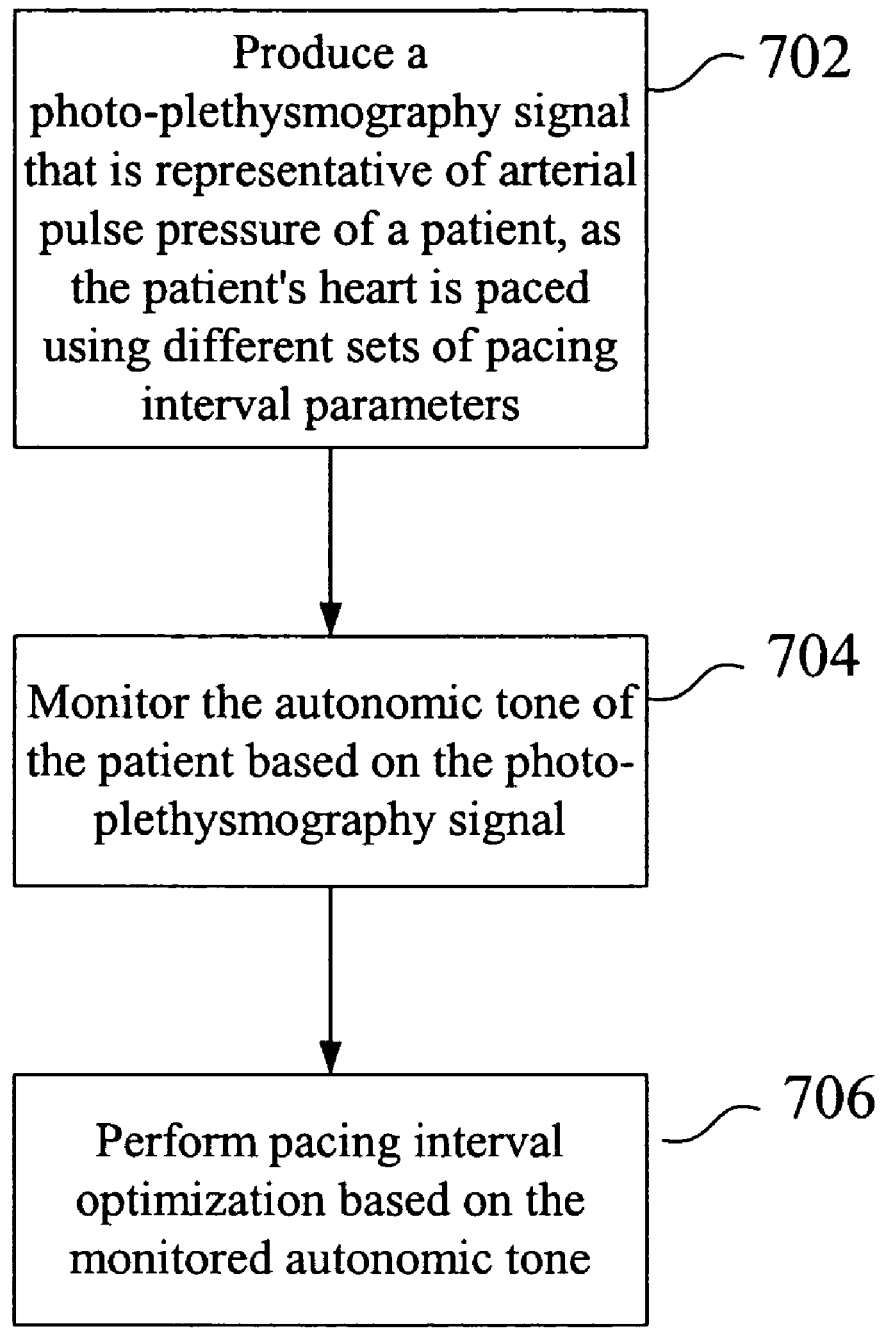
FIG. 24 is a flowchart that is useful for describing embodiments of the present invention, where measures of autonomic tone, produced using photo-plethysmography, are used for pacing interval optimization.

Now that an exemplary implantable stimulation device 510 has been described, the flowchart of FIG. 24 will be used to summarize how such a device can be used to perform pacing optimization, in accordance with embodiments of the present invention. More specifically, FIG. 24 describes how measures of autonomic tone, produced based on a photo-plethysmography signal, can be used to perform pacing optimization.

Referring to FIG. 24, at step 702, a photo-plethysmography signal, that is representative of arterial pulse pressure of the patient, is produced as a patient's heart is paced using different sets of pacing interval parameters. Each set of pacing interval parameters can include one or more pacing intervals (i.e., delays). The initiating event, from which the inter/delay is specified, can be either a delivered pace pulse, or a sensed depolarization. The pacing interval parameters can be used, e.g., for multi-site pacing, and may include an atrio-ventricular delay, an interventricular delay and/or an interatrial delay. Pacing intervals can define an intra-chamber pacing delay or an inter-chamber pacing delay. Pacing intervals can be used for two, three or four chamber pacing. These are just a few examples, which are not meant to limit the scope of the present invention.

At step 704, the autonomic tone of the patient is monitored, based on the photo-plethysmography signal. This can include, for example, obtaining measures of pulse amplitude from the photo-plethysmography signal.

At step 706, pacing interval optimization is performed based on the monitored autonomic tone. This can include, selecting one of the plurality of sets of pacing interval parameters, as a preferred set, based on the monitored autonomic tone. More specifically, since increases in cardiac performance have been found to coincide with decreases in sympathetic tone (and, thus, increases in parasympathetic tone), measures of sympathetic tone (or parasympathetic tone) can be used to select (or adjust) pacing interval parameters, in accordance with an embodiment of the present invention. As was described above, decreases in sympathetic tone (or increases in parasympathetic tone) can be recognized by increases in pulse amplitude and/or increases in pulse amplitude variability. Thus, where step 704 includes obtaining measures of pulse amplitude from a photo-plethysmography signal, step 706 can include selecting one of the plurality of sets of pacing interval parameters, corresponding to a greatest measure of pulse amplitude and/or a greatest measure of pulse amplitude variability, as a preferred set of pacing interval parameters. More generally, step 706 can include selecting the set of pacing interval parameters, corresponding to a minimum sympathetic tone (or maximum parasympathetic tone), as a preferred set of pacing interval parameters.

The photo-plethysmography signal produced at step 702 will likely be produced using a light source and a light detector that are incorporated with an extravascularly implanted stimulation device, similar to device 510, described above. This would allow pacing interval optimization to be performed after the device is implanted in a patient. Such optimization can occur once, continually, periodically, or aperiodically, for example. Alternatively, the light source and light detector used to produce the photo-plethysmography signal are not implanted in a patient, but are rather are placed on a finger, earlobe, or the like, of the patient. In such an embodiment, the autonomic tone of the patient can be monitored using the photo-plethysmography signal produced by the external light source and detector, and the monitored autonomic tone can then be used to program an implanted stimulation device that is used to provide pacing therapy.

The various sets of pacing interval parameters used to pace the patient's heart at step 702 can be predefined. In such an embodiment, step 706 may simply include selecting one of a plurality of predefined sets of pacing interval parameters as a preferred set, based on the measures of autonomic tone. Alternatively, evolutionary algorithms can be used to develop new sets of pacing interval parameters based on earlier used sets of pacing parameters. Such evolutionary algorithms typically adjust pacing interval parameters in an attempt to determine the set of pacing interval parameters that provide maximum cardiac performance for the patient. Accordingly, the pacing interval optimization performed at step 706 may include the use of evolutionary algorithms. More specifically, step 706 may include continually, periodically, or aperiodically, adjusting the sets of pacing interval parameters in an attempt to determine a best set (i.e., a set that provides maximum cardiac performance). The precise manner in which the sets of pacing interval parameters are defined is not important to the present invention, and thus the present invention should not be limited to those manners just discussed.

Figure 25:
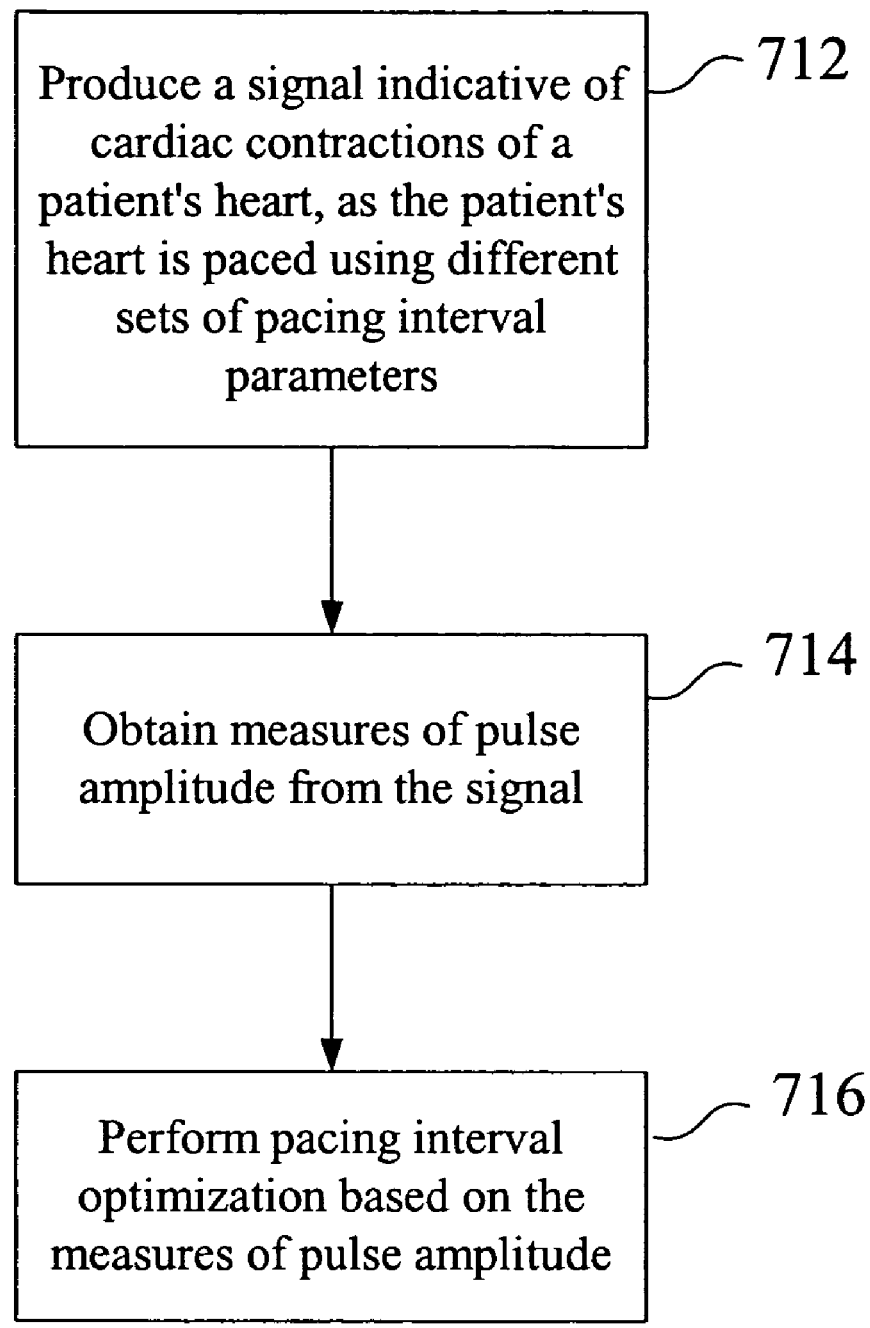
FIG. 25 is a flowchart that is useful for describing embodiments of the present invention in which pacing interval optimization is based on changes in pulse amplitude and/or pulse amplitude variability.

In accordance with further embodiments of the present invention, pacing interval optimization is performed based on measures of pulse amplitude that are obtained from a signal indicative of cardiac contractions of a patient's heart. More specifically, referring to FIG. 25, at step 712, a signal indicative of cardiac contractions of a patient's heart is produced, as the patient's heart is paced using different sets of pacing interval parameters. Such a signal may be a photo-plethysmography signal that is produced using an implanted or non-implanted light source and light detector, as has been discussed in detail above. The signal can alternatively be produced using a non-implanted pressure transducer (e.g., a strain gauge) that measures changes in blood pressure. In another embodiment, the signal is produced by an implanted transducer (e.g., a microphone or accelerometer) that detects heart sounds. In still another embodiment, an implanted pressure transducer is used to produce the signal. In a further embodiment, the signal is produced using an ultrasound transducer. Additional details of such transducers have been described above.

At step 714, measures of pulse amplitude are obtained from the signal. At step 716, pacing interval optimization is performed based on the measures of pulse amplitude. It is believed that increases in pulse amplitude and pulse amplitude variability are indicative of increases in cardiac performance. Accordingly, step 716 can include selecting one of the plurality of sets of pacing interval parameters, corresponding to a greatest measure of pulse amplitude and/or a greatest measure of pulse amplitude variability, as a preferred set of pacing interval parameters. As was discussed above, with reference to FIG. 24, the precise manner in which the various sets of pacing interval parameters is selected is not important to the present invention.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for monitoring autonomic tone of a patient, comprising:
   (a) producing a photo-plethysmography signal that is representative of arterial pulse pressure of the patient; and
   (b) monitoring the autonomic tone of the patient based on the photo-plethysmography signal by identifying changes in at least one of sympathetic tone and parasympathetic tone of the patient based on changes in pulse amplitude associated with the photo-plethysmography signal.

2. A method for monitoring autonomic tone of a patient, comprising:
   (a) producing a photo-plethysmography signal that is representative of arterial pulse pressure of the patient;
   (b) monitoring the autonomic tone of the patient based on the photo-plethysmography signal;
   (b.1) obtaining measures of pulse amplitude from the photo-plethysmography signal; and
   (b.2) identifying changes in sympathetic tone of the patient based changes in the measures of pulse amplitude.

3. The method of claim 2, wherein step (b.2) includes recognizing an increase in pulse amplitude as a decrease in the sympathetic tone of the patient.

4. The method of claim 2, wherein step (b.2) includes recognizing an increase in pulse amplitude variability as a decrease in the sympathetic tone of the patient.

5. The method of claim 2, wherein step (b.2) includes recognizing a decrease in pulse amplitude as an increase in the sympathetic tone of the patient.

6. The method of claim 2, wherein step (b.2) includes recognizing a decrease in pulse amplitude variability as an increase in the sympathetic tone of the patient.

7. A method for monitoring autonomic tone of a patient, comprising:
   (a) producing a photo-plethysmography signal that is representative of arterial pulse pressure of the patient;
   (b) monitoring the autonomic tone of the patient based on the photo-plethysmography signal;
   (b.1) obtaining measures of pulse amplitude from the photo-plethysmography signal; and
   (b.2) identifying changes in parasympathetic tone of the patient based changes in the measures of pulse amplitude.

8. The method of claim 7, wherein step (b.2) includes recognizing an increase in pulse amplitude as an increase in the parasympathetic tone of the patient.

9. The method of claim 7, wherein step (b.2) includes recognizing an increase in pulse amplitude variability as an increase in the parasympathetic tone of the patient.

10. The method of claim 7, wherein step (b.2) includes recognizing a decrease in pulse amplitude as a decrease in the parasympathetic tone of the patient.

11. The method of claim 7, wherein step (b.2) includes recognizing a decrease in pulse amplitude variability as a decrease in the parasympathetic tone of the patient.

12. A method for monitoring autonomic tone of a patient, comprising:
(a) producing a photo-plethysmography signal that is representative of arterial pulse pressure of the patient using a light source and a detector, that are extravascularly implanted in the patient, to produce the photo-plethysmography signal; and
(b) monitoring the autonomic tone of the patient based on the photo-plethysmography signal.

13. A system for monitoring autonomic tone of a patient, comprising:
a light source and a detector to produce a photo-plethysmography signal that is representative of arterial pulse pressure of a patient; and
a means for monitoring the autonomic tone of the patient based on the photo-plethysmography signal, wherein the means for monitoring autonomic tone is adapted to identify changes in at least one of sympathetic tone and parasympathetic tone of the patient based on changes in pulse amplitude associated with the photo-plethysmography signal.

14. A system for monitoring autonomic tone of a patient, comprising:
a light source and a detector to produce a photo-plethysmography signal that is representative of arterial pulse pressure of a patient; and
a means for monitoring the autonomic tone of the patient based on the photo-plethysmography signal, wherein the light source and the detector are incorporated into an implantable device.

15. A system for monitoring autonomic tone of a patient, comprising:
a light source and a detector to produce a photo-plethysmography signal that is representative of arterial pulse pressure of a patient; and
a means for monitoring the autonomic tone of the patient based on the photo-plethysmography signal, wherein the means for monitoring autonomic tone is adapted to recognize an increase in pulse amplitude variability as a decrease in the sympathetic tone of the patient.

16. A method for performing pacing interval optimization, comprising:
(a) producing a photo-plethysmography signal that is representative of arterial pulse pressure of the patient, as the patient's heart is paced using different sets of pacing interval parameters;
(b) monitoring the autonomic tone of the patient, based on the photo-plethysmography signal; and
(c) performing pacing interval optimization based on the monitored autonomic tone.

17. The method of claim 16, wherein step (c) includes selecting one of the plurality of sets of pacing interval parameters, as a preferred set, based on the monitored autonomic tone.

18. The method of claim 16, wherein:
step (b) includes obtaining measures of pulse amplitude from the photo-plethysmography signal; and
step (c) includes selecting one of the plurality of sets of pacing interval parameters, corresponding to a greatest measure of pulse amplitude, as a preferred set of pacing interval parameters.

19. The method of claim 16, wherein:
step (b) includes obtaining measures of pulse amplitude from the photo-plethysmography signal; and
step (c) includes selecting one of the plurality of sets of pacing interval parameters, corresponding to a greatest pulse amplitude variability, as a preferred set of pacing interval parameters.

20. The method of claim 16, wherein step (c) includes selecting the set of pacing interval parameters, corresponding to a minimum sympathetic tone, as a preferred set of pacing interval parameters.

21. The method of claim 16, wherein step (c) includes selecting the set of pacing interval parameters, corresponding to a maximum parasympathetic tone, as a preferred set of pacing interval parameters.

22. The method of claim 16, wherein each set of pacing interval parameters includes at least one pacing interval parameter, with an initiating event being either a delivered pace pulse or a sensed depolarization.

23. The method of claim 22, wherein each set of pacing interval parameters includes at least one of the following pacing interval parameters:
atrio-ventricular delay;
interventricular delay; and
interatrial delay.

24. The method of claim 22, wherein each set of pacing interval parameters includes a intra-chamber pacing delay.

25. The method of claim 22, wherein each set of pacing interval parameters defines pacing delays for dual-chamber pacing.

26. The method of claim 22, wherein each set of pacing interval parameters defines pacing delays for three chamber pacing.

27. The method of claim 22, wherein each set of pacing interval parameters defines pacing delays for four chamber pacing.

28. The method of claim 22, wherein each set of pacing interval parameters defines pacing delays for multi-site pacing.

29. The method of claim 16, wherein step (a) includes using a light source and a detector, that are extravascularly implanted in the patient, to produce the photo-plethysmography signal.

30. The method of claim 16, wherein step (a) includes using a light source and a detector, that are not implanted in the patient, to produce the photo-plethysmography signal.

31. A system for performing pacing interval optimization, comprising:
a pacing circuit to pace a patient's heart using different sets of pacing interval parameters;
a light source and a detector to produce a photo-plethysmography signal that is representative of arterial pulse pressure of a patient, as the patient's heart is paced using the different sets of pacing interval parameters; and
a processor adapted to monitor the autonomic tone of the patient based on the photo-plethysmography signal, and to perform pacing interval optimization based on the monitored autonomic tone.

32. The system of claim 31, wherein each set of pacing interval parameters includes at least one pacing interval parameter, with an initiating event being either a delivered pace pulse or a sensed depolarization.

33. The system of claim 32, wherein each set of pacing interval parameters includes at least one of the following pacing interval parameters:
- atrio-ventricular delay;
- interventricular delay; and
- interatrial delay.

34. A method for performing pacing interval optimization, comprising:
(a) producing a photo-plethysmography signal that is representative of arterial pulse pressure of the patient, as the patient's heart is paced using different sets of pacing interval parameters;
(b) performing pacing interval optimization by using measures of the photo-plethysmography signal as indicators of cardiac performance.

35. The method of claim 34, wherein the measures of the photo-plethysmography comprise amplitude measures.

36. The method of claim 34, wherein an increase in pulse amplitude is recognized as an indicator of an increase in cardiac performance.

37. The method of claim 34, wherein an increase in pulse amplitude variability is recognized as an indicator of an increase in cardiac performance.

38. The method of claim 34, wherein step (a) includes using a light source and a detector, that are extravascularly implanted in the patient, to produce the photo-plethysmography signal.

39. The method of claim 34, wherein step (a) includes using a light source and a detector, that are not implanted in the patient, to produce the photo-plethysmography signal.

* * * * *